US006500658B1

(12) United States Patent
Wu et al.

(10) Patent No.: US 6,500,658 B1
(45) Date of Patent: Dec. 31, 2002

(54) XYLOGLUCANASE FROM MALBRANCHEA

(75) Inventors: Wenping Wu, Beijing (CN); Martin Schulein, Copenhagen O (DK); Markus Sakari Kauppinen, Smorum (DK); Mary Ann Stringer, Copenhagen O (DK)

(73) Assignee: Novozymes, A/S, Bagsvaerd (DK)

( * ) Notice: Subject to any disclaimer, the term of this patent is extended or adjusted under 35 U.S.C. 154(b) by 0 days.

(21) Appl. No.: 09/653,778

(22) Filed: Sep. 1, 2000

Related U.S. Application Data

(63) Continuation of application No. PCT/DK00/00450, filed on Aug. 11, 2000.

(60) Provisional application No. 60/149,397, filed on Aug. 17, 1999.

(51) Int. Cl.[7] ........................... C12P 21/06; C12N 9/00; C12N 9/24; C12N 9/36

(52) U.S. Cl. ...................... 435/206; 435/69.1; 435/183; 435/200; 435/209; 435/262; 435/263; 435/264; 510/114

(58) Field of Search ................................ 435/183, 200, 435/206, 209, 226, 252.3, 69.1, 262, 263, 264; 510/114

(56) References Cited

PUBLICATIONS

Carpita et al, "Structural models of primary cell walls in flowering plants: consistency of molecular structure with the physical properties of the walls during growth", The Plant Journal (1993) 3(1), 1–30.

Rose et al, "Two Divergent Xyloglucan Endotransglycosylases Exhibit Mutally Exclusive Patterns of Expression in Nasturtium", Plant Physiol. (1996) 110: 493–499.

McDougall et al, "Fucosylated Xyloglucan in Suspension–Cultured cells of the Graminaceous Monocotyledon, *Festuca arundinacea*," J. Plant Physiol. vol. 143. pp. 591–595 (1994).

Ohsumi et al, "The Oligosaccharide Units of the Xyloglucans in the Cell Walls of Bulbs of Onion, Garlic and their Hybrid", Plant Cell Physiol. 35(6): 963–967 (1994).

Henrissat, Bernard, "A classification of glycosyl hydrolases based on amino acid sequence similarities", Biochem. J. (1991) 280, 309–316.

Hayashi et al, "Xyloglucan in the cell walls of cotton fiber", Carbohydrate Research, 181 (1988) 273–277.

Henrissat et al, "New families in the classification of glycosyl hydrolases based on amino acid sequence similarities", Biochem. J. (1993) 293, 781–788.

Fry et al, "Xyloglucan endotransglycosylase, a new wall–loosening enzyme activity from plants", Biochem. J. (1992) 282, 821–828.

Vincken et al, "Substrate specificity of endoglucanases: what determines xyloglucanase activity?", Carbohydrate Research 298 (1997) 299–310.

York et al, "The structures of arabinoxyloglucans produced by solanaceous plants", Carbohydrate Research 285 (1996) 99–128.

*Primary Examiner*—Rebecca E. Prouty
*Assistant Examiner*—Manjunath N. Rao
(74) *Attorney, Agent, or Firm*—Elias J. Lambiris; Jason I. Gorbell

(57) ABSTRACT

An isolated or purified polypeptide having xyloglucanase activity which is obtained from a strain of the genus Malbranchea and has xyloglucanase activity in the pH range 4–11, measured at 50° C.; and/or a molecular mass of 25±10 kDa, as determined by SDS-PAGE; and/or an isoelectric point (pI) in the range 3–5; and/or an N-terminal sequence Ala-Asp-Phe-Cys-Gly-Gln-Xaa-Asp-Ser-Glu-Gln-Ser-Gly-Pro-Tyr-Ile-Val-Tyr-Asn-Asn-Leu is useful in industrial applications such as in laundry detergent compositions and for treatment of textiles.

16 Claims, 4 Drawing Sheets

SEQUENCE LISTING

```
<160> NUMBER OF SEQ ID NOS: 19

<210> SEQ ID NO 1
<211> LENGTH: 1109
<212> TYPE: DNA
<213> ORGANISM: Malbranchea cinnamomea
<220> FEATURE:
<221> NAME/KEY: CDS
<222> LOCATION: (57)...(809)
<221> NAME/KEY: mat_peptide
<222> LOCATION: (141)...(806)
```

-continued

```
<400> SEQUENCE: 1

gctcaatttc tcgcggcatc aactattagc ctcaacgacc caacgataga gtcgag atg      59
                                                              Met
                                                                1

aag gtc gct gtt gca tcc ctt ctc ctt gct tct gcc gtc cca ggc atc      107
Lys Val Ala Val Ala Ser Leu Leu Leu Ala Ser Ala Val Pro Gly Ile
                5                  10                  15

ttt gcg cag ccc acc ggg agc ctt gag aaa cgg gcc gac ttt tgc ggg      155
Phe Ala Gln Pro Thr Gly Ser Leu Glu Lys Arg Ala Asp Phe Cys Gly
            20                  25                  30

caa tgg gac tcc gaa cag agc ggc ccg tat att gtc tac aat aat ctc      203
Gln Trp Asp Ser Glu Gln Ser Gly Pro Tyr Ile Val Tyr Asn Asn Leu
        35                  40                  45

tgg aat atg ggc aca ggt acg ggc tcg cag tgc acg gga gtc gac ggc      251
Trp Asn Met Gly Thr Gly Thr Gly Ser Gln Cys Thr Gly Val Asp Gly
    50                  55                  60                  65

att gat ggc tcg acg ctg gcg tgg cac acc agc tgg tcc tgg tcg gga      299
Ile Asp Gly Ser Thr Leu Ala Trp His Thr Ser Trp Ser Trp Ser Gly
                    70                  75                  80

ggg caa ggc caa gtc aag tcc tac gca aat gcc gtc ctt gca gac att      347
Gly Gln Gly Gln Val Lys Ser Tyr Ala Asn Ala Val Leu Ala Asp Ile
                85                  90                  95

gtc tcc aac cca cgc gcc atc tcc gac att aac agc atc ccc tcg acc      395
Val Ser Asn Pro Arg Ala Ile Ser Asp Ile Asn Ser Ile Pro Ser Thr
            100                 105                 110

tgg cgc tgg agc tac agc ggc agc tct ctc gtc gcc aac gtc gca tac      443
Trp Arg Trp Ser Tyr Ser Gly Ser Ser Leu Val Ala Asn Val Ala Tyr
        115                 120                 125

gac ctc ttt acc tcc tcc agc ccc tcg ggc tcc gag gag tac gag gtg      491
Asp Leu Phe Thr Ser Ser Ser Pro Ser Gly Ser Glu Glu Tyr Glu Val
    130                 135                 140                 145

atg atc tgg ctc gca gca ctg ggc ggc gcg ggc ccc atc tct gag aca      539
Met Ile Trp Leu Ala Ala Leu Gly Gly Ala Gly Pro Ile Ser Glu Thr
                    150                 155                 160

gga tcg ccg att gcg aac ccc acg gtt gcg ggg gtc aat tgg aat ttg      587
Gly Ser Pro Ile Ala Asn Pro Thr Val Ala Gly Val Asn Trp Asn Leu
                165                 170                 175

ttc gag ggg tac aac ggc aac atg cac gtg tac agc ttc gtg gct gcg      635
Phe Glu Gly Tyr Asn Gly Asn Met His Val Tyr Ser Phe Val Ala Ala
            180                 185                 190

ggt gga agt gtt gag aat ttc agt ggg gac ttg aag gat ttc ttg aac      683
Gly Gly Ser Val Glu Asn Phe Ser Gly Asp Leu Lys Asp Phe Leu Asn
        195                 200                 205

tat ttg ggg agc gag cag ggg atg gac cag agc cag tat gtg atc aat      731
Tyr Leu Gly Ser Glu Gln Gly Met Asp Gln Ser Gln Tyr Val Ile Asn
    210                 215                 220                 225

att ggc gcg gga aca gag ccg ttt agt ggt aat aat gcc gtc ttc acc      779
Ile Gly Ala Gly Thr Glu Pro Phe Ser Gly Asn Asn Ala Val Phe Thr
                    230                 235                 240

act tct gcg tat agc gtc cag gtt caa tag agaccgttgc cgagggcaac        829
Thr Ser Ala Tyr Ser Val Gln Val Gln  *
                245                 250

gggatctgaa gcgagtgacc acgaccggaa agattggatg agagtgagtt gtacgaaaga    889

gttttgcgaa tgcagggaaa agatccgctc gtggagaacc cttctgcatt cattcagtgc    949

acttcaaata tctgtcatga gatatgttgt aaatatcgat gtatcagtcc aggtcacacg   1009

cttcatgtgc gcgagagcat cgttaatcaa cttttttagc tctttggctc gcccaaaaaa   1069

aaaaaaaaaa aaaaaaaaaa aaaaaaaaaa aaaaaaaaaa                         1109
```

-continued

<210> SEQ ID NO 2
<211> LENGTH: 250
<212> TYPE: PRT
<213> ORGANISM: Malbranchea cinnamomea

<400> SEQUENCE: 2

```
Met Lys Val Ala Val Ala Ser Leu Leu Leu Ala Ser Ala Val Pro Gly
 1               5                  10                  15

Ile Phe Ala Gln Pro Thr Gly Ser Leu Glu Lys Arg Ala Asp Phe Cys
            20                  25                  30

Gly Gln Trp Asp Ser Glu Gln Ser Gly Pro Tyr Ile Val Tyr Asn Asn
        35                  40                  45

Leu Trp Asn Met Gly Thr Gly Thr Gly Ser Gln Cys Thr Gly Val Asp
    50                  55                  60

Gly Ile Asp Gly Ser Thr Leu Ala Trp His Thr Ser Trp Ser Trp Ser
65                  70                  75                  80

Gly Gly Gln Gly Gln Val Lys Ser Tyr Ala Asn Ala Val Leu Ala Asp
                85                  90                  95

Ile Val Ser Asn Pro Arg Ala Ile Ser Asp Ile Asn Ser Ile Pro Ser
            100                 105                 110

Thr Trp Arg Trp Ser Tyr Ser Gly Ser Ser Leu Val Ala Asn Val Ala
        115                 120                 125

Tyr Asp Leu Phe Thr Ser Ser Ser Pro Ser Gly Ser Glu Glu Tyr Glu
    130                 135                 140

Val Met Ile Trp Leu Ala Ala Leu Gly Gly Ala Gly Pro Ile Ser Glu
145                 150                 155                 160

Thr Gly Ser Pro Ile Ala Asn Pro Thr Val Ala Gly Val Asn Trp Asn
                165                 170                 175

Leu Phe Glu Gly Tyr Asn Gly Asn Met His Val Tyr Ser Phe Val Ala
            180                 185                 190

Ala Gly Gly Ser Val Glu Asn Phe Ser Gly Asp Leu Lys Asp Phe Leu
        195                 200                 205

Asn Tyr Leu Gly Ser Glu Gln Gly Met Asp Gln Ser Gln Tyr Val Ile
    210                 215                 220

Asn Ile Gly Ala Gly Thr Glu Pro Phe Ser Gly Asn Asn Ala Val Phe
225                 230                 235                 240

Thr Thr Ser Ala Tyr Ser Val Gln Val Gln
                245                 250
```

<210> SEQ ID NO 3
<211> LENGTH: 31
<212> TYPE: DNA
<213> ORGANISM: Artificial Sequence
<220> FEATURE:
<223> OTHER INFORMATION: Primer

<400> SEQUENCE: 3
ttgaattgaa aatagattga tttaaaactt c 31

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4

-continued ttgcatgcgt aatcatggtc atagc 25

<210> SEQ ID NO 5
<211> LENGTH: 26
<212> TYPE: DNA
<213> ORGANISM: Artificial Sequence
<220> FEATURE:
<223> OTHER INFORMATION: Primer

<400> SEQUENCE: 5
ttgaattcat gggtaataac tgatat 26

<210> SEQ ID NO 6
<211> LENGTH: 32
<212> TYPE: DNA
<213> ORGANISM: Artificial Sequence
<220> FEATURE:
<223> OTHER INFORMATION: Primer

<400> SEQUENCE: 6
aaatcaatct attttcaatt caattcatca tt 32

<210> SEQ ID NO 7
<211> LENGTH: 11
<212> TYPE: DNA
<213> ORGANISM: Artificial Sequence
<220> FEATURE:
<223> OTHER INFORMATION: Primer

<400> SEQUENCE: 7
gtactaaaac c 11

<210> SEQ ID NO 8
<211> LENGTH: 11
<212> TYPE: DNA
<213> ORGANISM: Artificial Sequence
<220> FEATURE:
<223> OTHER INFORMATION: Primer

<400> SEQUENCE: 8
ccgttaaatt t 11

<210> SEQ ID NO 9
<211> LENGTH: 45
<212> TYPE: DNA
<213> ORGANISM: Artificial Sequence
<220> FEATURE:
<223> OTHER INFORMATION: Primer

<400> SEQUENCE: 9
ggatgctgtt gactccggaa atttaacggt ttggtcttgc atccc 45

<210> SEQ ID NO 10
<211> LENGTH: 14
<212> TYPE: DNA
<213> ORGANISM: Artificial Sequence
<220> FEATURE:
<223> OTHER INFORMATION: Primer

<400> SEQUENCE: 10
atgcaattta aact 14

<210> SEQ ID NO 11
<211> LENGTH: 14
<212> TYPE: DNA
<213> ORGANISM: Artificial Sequence -continued
<220> FEATURE:
<223> OTHER INFORMATION: Primer

<400> SEQUENCE: 11
cggcaattta acgg 14

<210> SEQ ID NO 12
<211> LENGTH: 44
<212> TYPE: DNA
<213> ORGANISM: Artificial Sequence
<220> FEATURE:
<223> OTHER INFORMATION: Primer

<400> SEQUENCE: 12
ggtattgtcc tgcagacggc aatttaacgg cttctgcgaa tcgc 44

<210> SEQ ID NO 13
<211> LENGTH: 20
<212> TYPE: DNA
<213> ORGANISM: Artificial Sequence
<220> FEATURE:
<223> OTHER INFORMATION: Primer
<221> NAME/KEY: misc_feature
<222> LOCATION: 12
<223> OTHER INFORMATION: n = inosine

<400> SEQUENCE: 13
gayttytgyg gncartggga 20

<210> SEQ ID NO 14
<211> LENGTH: 23
<212> TYPE: DNA
<213> ORGANISM: Artificial Sequence
<220> FEATURE:
<223> OTHER INFORMATION: Primer
<221> NAME/KEY: misc_feature
<222> LOCATION: 3,15
<223> OTHER INFORMATION: n = inosine

<400> SEQUENCE: 14
tgnswytgrt ccatnccytg ytc 23

<210> SEQ ID NO 15
<211> LENGTH: 27
<212> TYPE: DNA
<213> ORGANISM: Artificial Sequence
<220> FEATURE:
<223> OTHER INFORMATION: Primer
<221> NAME/KEY: misc_feature
<222> LOCATION: 3,9,24
<223> OTHER INFORMATION: n = inosine

<400> SEQUENCE: 15
acngayatnc araaygarga rytntgg 27

<210> SEQ ID NO 16
<211> LENGTH: 27
<212> TYPE: DNA
<213> ORGANISM: Artificial Sequence
<220> FEATURE:
<223> OTHER INFORMATION: Primer

<400> SEQUENCE: 16
cgggatccga tagagtcgag atgaagg 27

<210> SEQ ID NO 17
<211> LENGTH: 29

-continued

```
<212> TYPE: DNA
<213> ORGANISM: Artificial Sequence
<220> FEATURE:
<223> OTHER INFORMATION: Primer

<400> SEQUENCE: 17

ccgctcgagc caaagagcta aaaaagttg                                29


<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18

gtttccaact caatttacct c                                        21


<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19

ttgccctcat ccccatcctt t                                        21
```

XYLOGLUCANASE FROM MALBRANCHEA

CROSS-REFERENCE TO RELATED APPLICATIONS

This application is a continuation of PCT/DK00/00450 filed on Aug. 11, 2000, and claims priority under 35 U.S.C. 119 of U.S. application No. 60/149,397 filed on Aug. 17, 1999, the contents of which are fully incorporated herein by reference.

The present invention relates to xyloglucanase enzymes which are endogeneous to a strain belonging to Malbranchea, especially enzymes exhibiting xyloglucanase activity in the pH range 4–11; to a method of producing such enzymes; and to use of such enzymes in the textile, detergent and cellulose fiber processing industries.

BACKGROUND OF THE INVENTION

Xyloglucan is a major structural polysaccharide in the primary (growing) cell wall of plants. Structurally, xyloglucans consists of a cellulose-like beta-1,4-linked glucose backbone which is frequently substituted with various side chains. The xyloglucans of most dicotyledonous plants, some monocotyledons and gymnosperms are highly branched polysaccharides in which approx. 75% of the glucose residues in the backbone bear a glycosyl side chain at O-6. The glycosyl residue that is directly attached to the branched glucose residue is invariably alfa-D-xylose. Up to 50% of the side chains in the xyloglucans contain more than one residue due to the presence of beta-D-galactose or alfa-L-fucose-(1-2)-beta-D-galactose moieties at O-2 of the xylose residues (C. Ohsumi and T. Hayashi (1994) Plant and Cell Physiology 35:963–967; G. J. McDougall and S. C. Fry (1994) Journal of Plant Physiology 143:591–595; J. L. Acebes et al. (1993) Phytochemistry 33:1343–1345). On acid hydrolysis, the xyloglucan extracted from cotton fibers yielded glucose, xylose, galactose and fucose in the ratio of 50:29:12:7 (Hayashi et al., 1988).

Xyloglucans produced by solanaceous plants are unusual in that typical only 40% of the beta-1,4-linked glucose residues bear a glycosyl side chain at O-6. Furthermore, up to 60% of the xylose residues are substituted at O-2 with alfa-L-arabinose residues and some solanaceous plants, such as potato, also have xyloglucans with beta-D-galactose substituents at O-2 of some of the xylose residues (York et al (1996)).

Xyloglucan is believed to function in the primary wall of plants by crosslinking cellulose-microfibrils, forming a cellulose-xyloglucan network. This network is considered necessary for the structural integrity of primary cell-walls (Carpita et al., 1993). Another important function of xyloglucan is to act as a repository for xyloglucan subunit oligo-saccharides that are physiologically active regulators of plant cell growth. Xyloglucan subunits may also modulate the action of a xyloglucan endotransglycosylase (XET), a cell-wall associated enzyme that has been hypothesized to play a role in the elongation of plant cell walls. Therefore xyloglucan might play an important role in wall loosening and consequently cell expansion (Fry et al., 1992).

The seeds of many dicotyledonous species contain xyloglucan as the major polysaccharide storage reserve. This type of xyloglucan, which is localized in massive thickenings on the inside of the seed cotyledon cell wall, is composed mainly of glucose, xylose and galactose (Rose et al., 1996).

Seeds of the tamarind tree *Tamarindus indica* became a commercial source of gum in 1943 when the gum was found useful as a paper and textile size. Sizing of jute and cotton with tamarind xyloglucan has been extensively practiced in Asia owing to the low cost of the gum and to its excellent properties. Food applications of tamarind xyloglucan include use in confections, jams and jellies and as a stabilizer in ice cream and mayonnaise (Whistler et al., 1993).

Xyloglucanase activity is not included in the classification of enzymes provided by the Enzyme Nomenclature (1992). Hitherto, this enzymatic activity has simply been classified as glucanase activity and has often been believed to be identical to cellulolytic activity (EC 3.2.1.4), i.e. activity against β-1,4-glycosidic linkages in cellulose or cellulose derivative substrates, or at least to be a side activity in enzymes having cellulolytic activity. However, a true xyloglucanase is a true xyloglucan specific enzyme capable of catalyzing the solubilisation of xyloglucan to xyloglucan oligosaccharides but which does not exhibit substantial cellulolytic activity, e.g. activity against the conventionally used cellulose-like substrates CMC (carboxymethylcellulose), HE cellulose and Avicel (microcrystalline cellulose). A xyloglucanase cleaves the beta-1,4-glycosidic linkages in the backbone of xyloglucan.

Xyloglucanase activity is described by Vincken et al. (1997) who characterizes three different endoglucanases from *Trichoderma viride* (similar to *T. reesei*) which all have high activity against cellulose or CMC and show that the EndoI (which is indeed belonging to family 5 of glycosyl hydrolases, see Henrissat, B. et al. (1991, 1993)) has essentially no (i.e. very little) activity against xyloglucan, and that EndoV (belonging to the family 7 of glycosyl hydrolases) and EndoIV (belonging to the family 12 of glycosyl hydrolases) both have activity against xyloglucan and CMC, respectively, of the same order of magnitude.

International Patent Publication WO 94/14953 discloses a xyloglucanase (EG II) cloned from the fungus *Aspergillus aculeatus.*

International Patent Publication WO 98/38288 discloses amino acid sequences of xyloglucanases from *Tiarosporella phaseolina* and *Dichotomocladium hesseltinei*, respectively.

International Patent Publication WO 98/50513 discloses laundry and cleaning compositions containing xyloglucanase enzymes.

International Patent Publication WO 99/02663 discloses xyloglucanases cloned from *Bacillus licheniformis* and *Bacillus agaradhaerens.*

Since many important processes, both industrial processes and domestic processes using industrially produced agents, are operating at a high pH in the alkaline range. Accordingly, there is a need for a true xyloglucanase enzyme with a high xyloglucanase activity at an alkaline pH.

SUMMARY OF THE INVENTION

The inventors have now found enzymes having substantial xyloglucanase activity at high pH in the alkaline range, such enzymes being obtained from or endogenous to a strain belonging to the fungal genus Malbranchea.

Accordingly, the present invention relates to an isolated or purified xyloglucanase enzyme obtained from a strain belonging to the genus Malbranchea, preferably to a strain belonging to a species selected from the group consisting of *Malbranchea cinnamomea* (and the three synonyms *Malbranchea sulfurea, Malbranchea pulchella* var. *sulfurea* and *Thermoidium sulfureum*), *Malbranchea graminicola, Malbranchea pulchella, Malbranchea filamentosa, Malbranchea gypsea, Malbranchea albolutea, Malbranchea*

*arcuata, Malbranchea aurantiaca, Malbranchea bolognesii-chiurcoi, Malbranchea chrysosporioidea, Malbranchea circinata, Malbranchea flava, Malbranchea flavorosea, Malbranchea flocciformis, Malbranchea fulva, Malbranchea kambayashii, Malbranchea multicolor, Malbranchea sclerotica, Malbranchea setosa* and *Malbranchea dendritica*, which enzyme exhibits xyloglucanase activity and no activity on cellulose or cellulose derivative substrates. In a preferred embodiment of the invention, the xyloglucanase has an apparent molecular weight of 25±10 kDa, a pI between 3 and 5 and exhibits xyloglucanase activity the pH range 4–11, measured at 50° C.

In a further aspect, the present invention provides a xyloglucanase cloned from a strain belonging to Malbranchea, i.e. a xyloglucanase selected from one of (a) a polypeptide comprising a fragment encoded by the DNA sequence of positions 141–806 of SEQ ID NO:1; (b) a polypeptide produced by culturing a cell comprising the sequence of SEQ ID NO:1 under conditions wherein the DNA sequence is expressed; and (c) a xyloglucanase enzyme having a sequence of at least 80% identity to positions 1–222 of SEQ ID NO:1 when identity is determined by GAP provided in the GCG program package verion 10.0 using a GAP creation penalty of 8 and GAP extension penalty of 2.

In another aspect, the present invention provides an isolated or purified polypeptide having xyloglucanase activity which is obtained from a strain of the genus Malbranchea and has i) xyloglucanase activity in the pH range 4–11, measured at 50° C.;

ii) a molecular mass of 25±10 kDa, as determined by SDS-PAGE;

iii) an isoelectric point (pI) in the range 3–5; and/or iv) the N-terminal sequence Ala-Asp-Phe-Cys-Gly-Gln-Trp-Asp-Ser-Glu-Gln-Ser-Gly-Pro-Tyr-Ile-Val-Tyr-Asn-Asn-Leu (SEQ ID NO: 2).

The invention further provides an isolated xyloglucanase enzyme which is (i) free from homologous impurities, and (ii). produced by culturing a cell comprising the DNA sequence of positions 141–806 of SEQ ID NO:1.

The novel enzyme of the present invention is useful for the treatment of cellulosic material, especially cellulose-containing fiber, yarn, woven or non-woven fabric. The treatment can be carried out during the processing of cellulosic material into a material ready for garment manufacture or fabric manufacture, e.g. in the desizing or scouring step; or during industrial or household laundering of such fabric or garment.

Accordingly, in further aspects the present invention relates to a detergent composition comprising a xyloglucanase which is endogeneous to a strain belonging to the fungal genus Malbranchea, in particular belonging to the fungal species *Malbranchea cinnomomea*, and exhibits substantial activity in the alkaline pH range; and to use of the enzyme of the invention for the treatment of cellulose-containing fibers, yarn, woven or non-woven fabric.

The present invention has now made it possible to use a truly enzymatic scouring process in the preparation of cellulosic material e.g. for proper response in subsequent dyeing operations. Further, it is contemplated that detergent compositions comprising the novel enzyme are capable of removing or bleaching certain soils or stains present on laundry, especially soils and spots resulting from xyloglucan-containing food, plants, and the like. It is also contemplated that treatment with detergent compositions comprising the novel enzyme can prevent binding of certain soils to the xyloglucan left on the cellulosic material.

THE DRAWINGS

In the accompanying drawings.

DETAILED DESCRIPTION OF THE INVENTION

Figure 1:
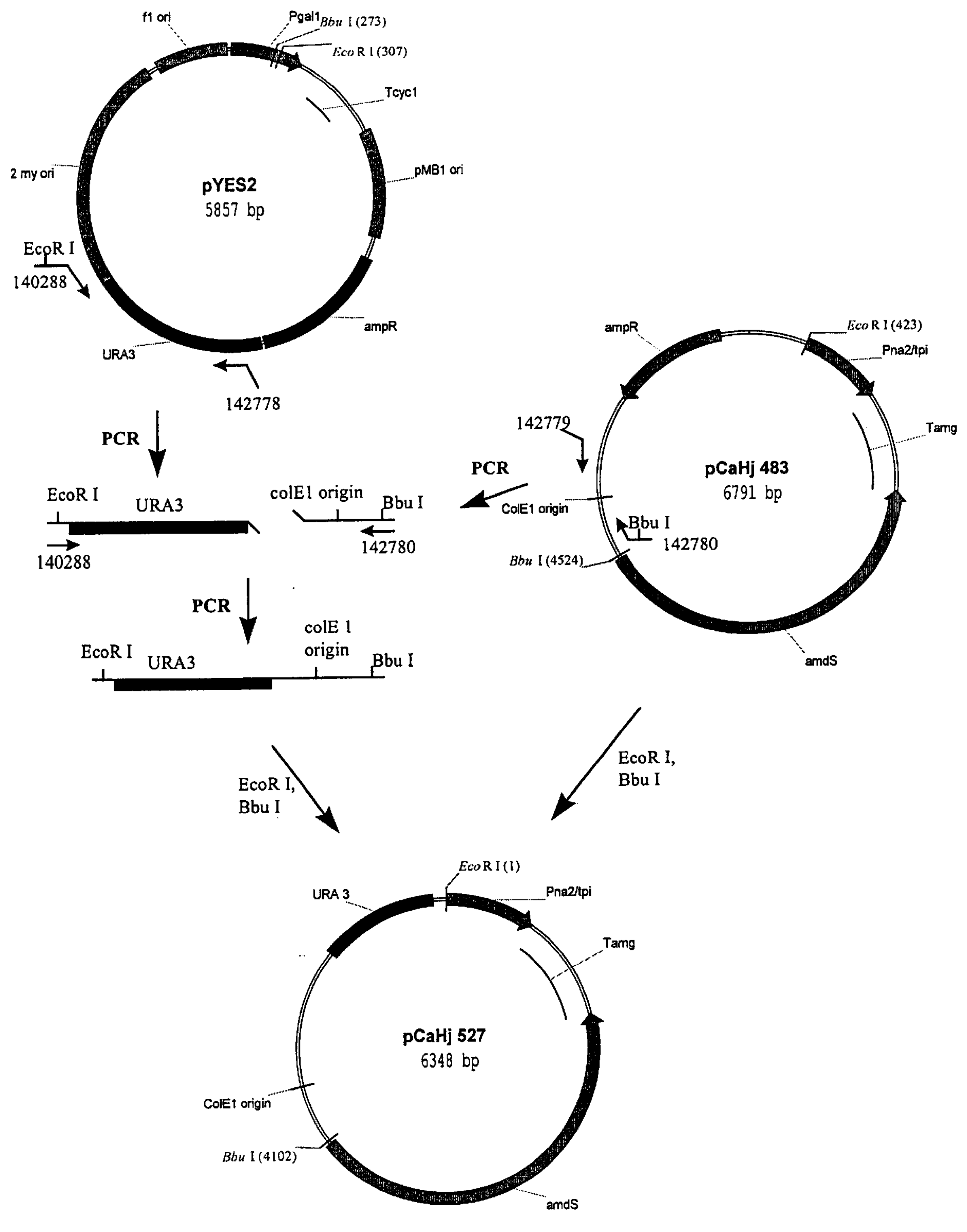
FIG. 1 shows construction of pCaHj 527.

Cellulases are found in more than 10 different families of glycosyl hydrolases. Some of the cellulases also exhibit xyloglucanase activity. Today, such cellulases have been found among those classified in the families 5, 7 and 12. The substrate specificity is, however, not directly correlated with the family: within a family the main enzymatic activity can be cellulase or mannanase (family 5), or lichinase, β-1,3-glucanase or xyloglucantransferase activity (family 16). Only very few enzymes are hitherto disclosed as having activity against xyloglucan as the major or main enzymatic activity. As mentioned above, this activity has not yet an entry in the official Enzyme Nomenclature.

In the present context, the term "enzyme preparation" is intended to mean either be a conventional enzymatic fermentation product, possibly isolated and purified, from a single species of a microorganism, such preparation usually comprising a number of different enzymatic activities; or a mixture of monocomponent enzymes, preferably enzymes derived from bacterial or fungal species by using conventional recombinant techniques, which enzymes have been fermented and possibly isolated and purified separately and which may originate from different species, preferably fungal or bacterial species; or the fermentation product of a microorganism which acts as a host cell for expression of a recombinant xyloglucanase, but which microorganism simultaneously produces other enzymes, e.g. xyloglucanases, proteases, or cellulases, being naturally occurring fermentation products of the microorganism, i.e. the enzyme complex conventionally produced by the corresponding naturally occurring microorganism.

In a preferred embodiment, the xyloglucanase of the invention has a relative activity at pH 9.5 of at least 50%, preferably at least 55%, more preferably at least 60%, especially at least 65%, in particular at least 70%, compared to the activity at the optimal pH.

In another preferred embodiment, the xyloglucanase of the invention has a relative activity at pH 10 of at least 40%, preferably at least 50%, more preferably at least 55%, especially at least 60%, compared to the activity at the optimal pH.

In another preferred embodiment the xyloglucanase of the invention is active at a temperature between 20° C. and 70° C. Preferably, the xyloglucanase has a relative activity in the temperature range 40–60° C. of at least 40%, more preferably at least 50%, especially at least 55%, in particular at least 60%, compared to the activity at the optimal temperature.

The xyloglucanase of the present invention exhibits no activity on cellulose or cellulose derivative substrates. A conventional substrate for determining cellulase activity (endo-β-1,4-glucanase activity, jf. EC 3.2.1.4) is carboxymethylcellulose (CMC). Another conventional substrate for determining cellulase or cellobiohydrolase activity (EC 3.2.1.91) is Avicel which is a micro-crystalline cellulose well known by the person skilled in the art.

The present invention also relates to an enzyme preparation comprising the xyloglucanase described herein, optionally further comprising one or more enzymes selected from the group consisting of proteases, cellulases (endo-β-1,4-glucanases), β-glucanases (endo-β-1,3(4)-glucanases), lipases, cutinases, peroxidases, laccases, amylases, glucoamylases, pectinases, reductases, oxidases, phenoloxidases, ligninases, pullulanases, arabinanases, hemicellulases, mannanases, galactanases, xylanases, pectin acetyl esterases, rhamnogalacturonan acetyl esterases, polygalacturonases, rhamnogalacturonases, pectin lyases, pectate lyases, pectin methylesterases, cellobiohydrolases, transglutaminases; or mixtures thereof. In a preferred embodiment, one or more or all enzymes in the preparation is produced by using recombinant techniques, i.e. the enzyme(s) is/are mono-component enzyme(s) which is/are mixed with the other enzyme(s) to form an enzyme preparation with the desired enzyme blend.

In another aspect, the present invention also relates to a method of producing the xyloglucanase or xyloglucanase preparation of the invention, the method comprising culturing a microorganism, eg a strain of the fungal genus Malbranchea, preferably a strain belonging to the species *Malbranchea cinnamomea* (and the three synonyms *Malbranchea sulfurea, Malbranchea pulchella* var. *sulfurea* and *Thermoidium sulfureum*), *Malbranchea graminicola, Malbranchea pulchella, Malbranchea filamentosa, Malbranchea gypsea, Malbranchea albolutea, Malbranchea arcuata, Malbranchea aurantiaca, Malbranchea bolognesii-chiurcoi, Malbranchea chrysosporioidea, Malbranchea circinata, Malbranchea flava, Malbranchea flavorosea, Malbranchea flocciformis, Malbranchea fulva, Malbranchea kambayashii, Malbranchea multicolor, Malbranchea sclerotica, Malbranchea setosa* and *Malbranchea dendritica*, for example a strain selected from the group consisting of *Malbranchea cinnamomea*, CBS 115.68, MUCL 11291, CBS 343.55, MUCL 9500, UAMH 3827, CBS 423.54, CBS 960.72 and UAMH 2485, which microorganism is capable of producing the xyloglucanase under conditions permitting the production of the enzyme, and recovering the enzyme from the culture. Culturing may be carried out using conventional fermentation techniques, e.g. culturing in shake flasks or fermentors with agitation to ensure sufficient aeration on a growth medium inducing production of the xyloglucanase enzyme. The growth medium may contain a conventional N-source such as peptone, yeast extract or casamino acids, a reduced amount of a conventional C-source such as dextrose or sucrose, and an inducer such as xyloglucan or composit plant substrates such as cereal brans (e.g. wheat bran or rice husk). The recovery may be carried out using conventional techniques, e.g. separation of bio-mass and supernatant by centrifugation or filtration, recovery of the supernatant or disruption of cells if the enzyme of interest is intracellular, perhaps followed by further purification as described in EP 0 406 314 or by crystallization as described in WO 97/15660.

In the present context the term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. The expression vector of the invention may be any expression vector that is conveniently subjected to recombinant DNA procedures, and the choice of vector will often depend on the host cell into which the vector is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The term "recombinant expressed" or "recombinantly expressed" used herein in connection with expression of a polypeptide or protein is defined according to the standard definition in the art. Recombinantly expression of a protein is generally performed by using an expression vector as described immediately above.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985). The term "an isolated polynucleotide" may alternatively be termed "a cloned polynucleotide".

When applied to a protein/polypeptide, the term "isolated" indicates that the protein is found in a condition other than its native environment. In a preferred form, the isolated protein is substantially free of other proteins, particularly other homologous proteins (i.e. "homologous impurities" (see below)). It is preferred to provide the protein in a greater than 40% pure form, more preferably greater than 60% pure form.

Even mote preferably it is preferred to provide the protein in a highly purified form, i.e., greater than 80% pure, more preferably greater than 95% pure, and even more preferably greater than 99% pure, as determined by SDS-PAGE.

The term "isolated protein/polypeptide may alternatively be termed "purified protein/polypeptide".

The term "homologous impurities" means any impurity (e.g. another polypeptide than the polypeptide of the invention) which originate from the homologous cell where the polypeptide of the invention is originally obtained from.

The term "obtained from" as used herein in connection with a specific microbial source, means that the polynucleotide and/or polypeptide produced by the specific source, or by a cell in which a gene from the source have been inserted.

The term "operably linked", when referring to DNA segments, denotes that the segments are arranged so that they function in concert for their intended purposes, e.g. transcription initiates in the promoter and proceeds through the coding segment to the terminator The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "complements of polynucleotide molecules" denotes polynucleotide molecules having a complementary base sequence and reverse orientation as compared to a reference sequence. For example, the sequence 5' ATGCACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

Polynucleotides

Within preferred embodiments of the invention an isolated polynucleotide of the invention will hybridize to similar sized regions of SEQ ID NO:1 or a sequence complementary thereto, under at least medium stringency conditions.

In particular polynucleotides of the invention will hybridize to a denatured double-stranded DNA probe comprising either the full sequence shown in SEQ ID NO:1 or the sequence shown in positions 141–806 of SEQ ID NO:1 or any probe comprising a subsequence of SEQ ID NO:1 having a length of at least about 100 base pairs under at least medium stringency conditions, but preferably at high stringency conditions as described in detail below. Suitable experimental conditions for determining hybridization at medium or high stringency between a nucleotide probe and a homologous DNA or RNA sequence involve presoaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5×Denhardt's solution (Sambrook et al. 1989), 0.5% SDS and 100 $\mu$g/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) Anal. Biochem. 132:6–13), 32P-dCTP-labeled (specific activity higher than 1×109 cpm/$\mu$g) probe for 12 hours at ca. 45° C. The filter is then washed twice for 30 minutes in 2×SSC, 0.5% SDS at least 60° C. (medium stringency), still more preferably at least 65° C. (medium/high stringency), even more preferably at least 70° C. (high stringency), and even more preferably at least 75° C. (very high stringency).

Molecules to which the oligonucleotide probe hybridizes under these conditions are detected using a x-ray film.

As previously noted, such isolated polynucleotides include DNA and RNA. Methods for isolating DNA and RNA are well known in the art. DNA and RNA encoding genes of interest can be cloned in Gene Banks or DNA libraries by means of methods known in the art.

Polynucleotides encoding polypeptides having xyloglucanase activity are then identified and isolated by, for example, hybridization or PCR.

Further, it is contemplated that counterpart polypeptides and polynucleotides from different fungal strains (orthologs or paralogs) can be provided.

Species homologues of a polypeptide with xyloglucanase activity can be cloned using information and compositions provided from the cloning of the Malbranchea xyloglucanase of the present invention in combination with conventional cloning techniques. For example, a DNA sequence can be cloned using chromosomal DNA obtained from a cell type that expresses the protein. Suitable sources of DNA can be identified by probing Northern blots with probes designed from the Malbranchea xyloglucanase DNA and polypeptide sequences when available. A library is then prepared from chromosomal DNA of a positive cell line. A DNA sequence encoding an polypeptide having xyloglucanase activity can then be isolated by a variety of methods, such as by probing with probes designed from the abovementioned sequences or with one or more sets of degenerate probes based on these sequences. A DNA sequence can also be cloned using the polymerase chain reaction, or PCR (Mullis, U.S. Pat. No. 4,683,202), using primers designed from the abovementioned sequences. Within an additional method, the DNA library can be used to transform or transfect host cells, and expression of the DNA of interest can be detected with an antibody (monoclonal or polyclonal) raised against a xyloglucanase cloned from *Malbranchea cinnamomea*, CBS 115.68, MUCL 11291, CBS 343.55, MUCL 9500, UAMH 3827, CBS 423.54, CBS 960.72 or UAMH 2485, expressed and purified, or by an activity test relating to a polypeptide having xyloglucanase activity.

Polypeptides

The sequence of amino acids nos. 29–250 of SEQ ID NO: 2 is believed to be a mature xyloglucanase, the N-terminal sequence starts at position 29 of SEQ ID NO:2.

The present invention also provides xyloglucanase polypeptides that are substantially homologous to the polypeptide of amino acids nos. 1–250 or 29–250 of SEQ ID NO:2 and species homologs (paralogs or orthologs) thereof. The term "substantially homologous" is used herein to denote polypeptides having 70%, preferably at least 75%, more preferably at least 80%, more preferably at least 85%, and even more preferably at least 90%, sequence identity to the sequence shown in amino acids nos. 1–250 or 29–250 of SEQ ID NO:2 or their orthologs or paralogs. Such polypeptides will more preferably be at least 95% identical, and most preferably 98% or more identical to the sequence shown in amino acids nos. 1–250 or 29–250 of SEQ ID NO:2 or its orthologs or paralogs.

Percent sequence identity is determined by conventional methods, by means of computer programs known in the art such as GAP provided in the GCG program package (Program Manual for the Wisconsin Package, Version 10.0, Genetics Computer Group, 575 Science Drive, Madison, Wis., USA 53711). GAP is used with the following settings for polypeptide sequence comparison: GAP creation penalty of 8 and GAP extension penalty of 2.

The deduced amino acid sequence of the XYG1011-encoded family 12 xyloglucanase precursor from *Malbranchea cinnamomea* (SEQ ID NO:2) shows 49.1–66.2% sequence similarity, and 43.9–61.2% sequence identity to a selection of 7 fungal family 12 enzymes. The sequences were aligned using the GAP program of the GCG Wisconsin software package, version 10.0 Genetics Computer Group (GCG), Madison, Wis.; with a gap creation penalty of 8, and a gap extension penalty of 2;

| | *Malbranchea cinnamomea* |
|---|---|
| *Tiasporella phaseolina*, w68593 | 66.2% similarity<br>61.2% identity |
| *Aspergillus aculeatus*, o94218 | 65.4% similarity<br>58.7% identity |
| *Emericella desertoru*, y06366 | 57.3% similarity<br>52.4% identity |
| *Gliocladium roseum*, y06362 | 58.9% similarity<br>54.5% identity |
| *Fusarium javanicum*, y06359 | 61.7% similarity<br>55.0% identity |
| *Myceliophthora thermophila*, w23540 | 50.0% similarity<br>46.7% identity |
| *Trichoderma reesei*, y06330 | 49.1% similarity<br>43.9% identity |

Substantially homologous proteins and polypeptides are characterized as having one or more amino acid substitutions, deletions or additions. These changes are preferably of a minor nature, that is conservative amino acid substitutions (see Table 2) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991. See, in general Ford et al., *Protein Expression and Purification* 2: 95–107, 1991, which is incorporated herein by reference. DNAs encoding affinity tags are available from commercial suppliers (e.g., Pharmacia Biotech, Piscataway, N.J.; New England Biolabs, Beverly, Mass.).

However, even though the changes described above preferably are of a minor nature, such changes may also be of a larger nature such as fusion of larger polypeptides of up to 300 amino acids or more both as amino- or carboxyl-terminal extensions to a polypeptide of the invention having xyloglucanase activity.

TABLE 1

| Conservative amino acid substitutions | |
|---|---|
| Basic: | arginine<br>lysine<br>histidine |
| Acidic: | glutamic acid<br>aspartic acid |
| Polar: | glutamine<br>asparagine |
| Hydrophobic: | leucine<br>isoleucine<br>valine |
| Aromatic: | phenylalanine<br>tryptophan<br>tyrosine |
| Small: | glycine<br>alanine<br>serine<br>threonine<br>methionine |

In addition to the 20 standard amino acids, non-standard amino acids (such as 4-hydroxyproline, 6-N-methyl lysine, 2-aminoisobutyric acid, isovaline and a-methyl serine) may be substituted for amino acid residues of a polypeptide according to the invention. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the xyloglucanase polypeptides of the present invention can be identified according to procedures known in the art, such as site-directed mutagenesis or alanine-scanning mutagenesis (Cunningham and Wells, *Science* 244: 1081–1085, 1989). In the latter technique, single alanine mutations are introduced at every residue in the molecule, and the resultant mutant molecules are tested for biological activity (i.e xyloglucanase activity) to identify amino acid residues that are critical to the activity of the molecule. See also, Hilton et al., *J. Biol. Chem.* 271:4699–4708, 1996. The active site of the enzyme or other biological interaction can also be determined by physical analysis of structure,.as determined by such techniques as nuclear magnetic resonance, crystallography, electron diffraction or photoaffinity labeling, in conjunction with mutation of putative contact site amino acids. See, for example, de Vos et al., *Science* 255:306–312, 1992; Smith et al., *J. Mol. Biol.* 224:899–904, 1992; Wlodaver et al., *FEBS Lett.* 309:59–64, 1992. The identities of essential amino acids can also be inferred from analysis of homologies with polypeptides which are related to a polypeptide according to the invention.

Multiple amino acid substitutions can be made and tested using known methods of mutagenesis, recombination and/or shuffling followed by a relevant screening procedure, such as those disclosed by Reidhaar-Olson and Sauer (*Science* 241:53–57, 1988), Bowie and Sauer (*Proc. Natl. Acad. Sci. USA* 86:2152–2156, 1989), WO95/17413, or WO 95/22625. Briefly, these authors disclose methods for simultaneously randomizing two or more positions in a polypeptide, or recombination/shuffling of different mutations (WO95/17413, WO95/22625), followed by selecting for functional a polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., DNA 7:127, 1988).

Mutagenesis/shuffling methods as disclosed above can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous the amino acid sequence of the Malbranchea xyloglucanase of the present invention and retain the xyloglucanase activity of the wild-type protein.

The xyloglucanase enzyme of the invention may, in addition to the enzyme core comprising the catalytically domain, also comprise a cellulose binding domain (CBD), the cellulose binding domain and enzyme core (the catalytically active domain) of the enzyme being operably linked. The cellulose binding domain (CBD) may exist as an integral part the encoded enzyme, or a CBD from another origin may be introduced into the xyloglucanase thus creating an enzyme hybride. In this context, the term "cellulose-binding domain" is intended to be understood as defined by Peter Tomme et al. "Cellulose-Binding Domains: Classification and Properties" in "Enzymatic Degradation of Insoluble Carbohydrates", John N. Saddler and Michael H. Penner (Eds.), ACS Symposium Series, No. 618, 1996. This definition classifies more than 120 cellulose-binding domains into 10 families (I–X), and demonstrates that CBDs are found in various enzymes such as cellulases, xylanases, mannanases, arabinofuranosidases, acetyl esterases and chitinases. CBDs have also been found in algae, e.g. the red alga Porphyra purpurea as a non-hydrolytic polysaccharide-binding protein, see Tomme et al., Op.cit. However, most of the CBDs are from cellulases and xylanases, CBDs are found at the N and C termini of proteins or are internal. Enzyme hybrids are known in the art, see e.g. WO 90/00609 and WO 95/16782, and may be prepared by transforming into a host cell a DNA construct comprising at least a fragment of DNA encoding the cellulose-binding domain ligated, with or without a linker, to a DNA sequence encoding the xyloglucanase and growing the host cell to express the fused gene. Enzyme hybrids may be described by the following formula:

CBD-MR-X wherein CBD is the N-terminal or the C-terminal region of an amino acid sequence corresponding to at least the cellulose-binding domain; MR is the middle region (the linker), and may be a bond, or a short linking group preferably of from about 2 to about 100 carbon atoms, more preferably of from 2 to 40 carbon atoms; or is preferably from about 2 to about 100 amino acids, more preferably of from 2 to 40 amino acids; and X is an N-terminal or C-terminal region of a polypeptide encoded by the polynucleotide molecule of the invention.

The Xyloglucan Substrate

In addition to the aforesaid about xyloglucan it should be noted that xyloglucan from tamarind seeds supplied by Megazyme, Ireland, has a complex branched structure with glucose, xylose, galactose and arabinose in the ratio of 45:36:16:3. Accordingly, it is strongly believed that an enzyme showing catalytic activity on this xyloglucan also has catalytic activity on other xyloglucan structures from different sources (angiosperms ot gymnosperms).

Use in the Detergent Industry

During washing and wearing, dyestuff from dyed fabrics or garment will conventionally bleed from the fabric which then looks faded and worn. Removal of surface fibers from the fabric will partly restore the original colours and looks of the fabric. By the term "colour clarification", as used herein, is meant the partly restoration of the initial colours of fabric or garment throughout multiple washing cycles.

The term "de-pilling" denotes removing of pills from the fabric surface.

The term "soaking liquor" denotes an aqueous liquor in which laundry may be immersed prior to being subjected to a conventional washing process. The soaking liquor may contain one or more ingredients conventionally used in a washing or laundering process.

The term "washing liquor" denotes an aqueous liquor in which laundry is subjected to a washing process, i.e. usually a combined chemical and mechanical action either manually or in a washing machine. Conventionally, the washing liquor is an aqueous solution of a powder or liquid detergent composition.

The term "rinsing liquor" denotes an aqueous liquor in which laundry is immersed and treated, conventionally immediately after being subjected to a washing process, in order to rinse the laundry, i.e. essentially remove the detergent solution from the laundry. The rinsing liquor may contain a fabric conditioning or softening composition.

The laundry subjected to the method of the present invention may be conventional washable laundry. Preferably, the major part of the laundry is sewn or unsewn fabrics, including knits, wovens, denims, yarns, and toweling, made from cotton, cotton blends or natural or manmade cellulosics (e.g. originating from xylan-containing cellulose fibers such as from wood pulp) or blends thereof. Examples of blends are blends of cotton or rayon/viscose with one or more companion material such as wool, synthetic fibers (e.g. polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g. rayon/viscose, ramie, flax/linen, jute, cellulose acetate fibers, lyocell).

DETERGENT DISCLOSURE AND EXAMPLES

Surfactant System

The detergent compositions according to the present is invention comprise a surfactant system, wherein the surfactant can be selected from nonionic and/or anionic and/or cationic and/or ampholytic and/or zwitterionic and/or semi-polar surfactants.

The surfactant is typically present at a level from 0.1% to 60% by weight.

The surfactant is preferably formulated to be compatible with enzyme components present in the composition. In liquid or gel compositions the surfactant is most preferably formulated in such a way that it promotes, or at least does not degrade, the stability of any enzyme in these compositions.

Preferred systems to be used according to the present inven-tion comprise as a surfactant one or more of the nonionic and/or anionic surfactants described herein.

Polyethylene, polypropylene, and polybutylene oxide conden-sates of alkyl phenols are suitable for use as the nonionic surfactant of the surfactant systems of the present inven-tion, with the polyethylene oxide condensates being preferred. These compounds include the condensation products of alkyl phenols having an alkyl group containing from about 6 to about 14 carbon atoms, preferably from about 8 to about 14 carbon atoms, in either a straight chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available nonionic surfactants of this type include Igepal™ CO-630, marketed by the GAF Corporation; and Triton™ X-45, X-114, X-100 and X-102, all marketed by the Rohm & Haas Company. These surfactants are commonly referred to as alkylphenol alkoxylates (e.g., alkyl phenol ethoxylates).

The condensation products of primary and secondary aliphatic alcohols with about 1 to about 25 moles of ethylene oxide are suitable for use as the nonionic surfactant of the nonionic surfactant systems of the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 2 to about 10 moles of ethylene oxide per mole of alcohol. About 2 to about 7 moles of ethylene oxide and most preferably from 2 to 5 moles of ethylene oxide per mole of alcohol are present in said condensation products. Examples of commercially available nonionic surfactants of this type include Tergitol™ 15-S-9 (The condensation product of $C_{11}$–$C_{15}$ linear alcohol with 9 moles ethylene oxide), Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45-9 (the condensation product of $C_{14}$–$C_{15}$ linear alcohol with 9 moles of ethylene oxide), Neodol™ 23-3 (the condensation product of $C_{12}$–$C_{13}$ linear alcohol with 3.0 moles of ethylene oxide), Neodol™ 45-7 (the condensation product of $C_{14}$–$C_{15}$ linear alcohol with 7 moles of ethylene oxide), Neodol™ 45-5 (the condensation product of $C_{14}$–$C_{15}$ linear alcohol with 5 moles of ethylene oxide) marketed by Shell Chemical Company, Kyro™ EOB (the condensation product of $C_{13}$–$C_{15}$ alcohol with 9 moles ethylene oxide), marketed by The Procter & Gamble Company, and Genapol LA 050 (the condensation product of $C_{12}$–$C_{14}$ alcohol with 5 moles of ethylene oxide) marketed by Hoechst. Preferred range of HLB in these products is from 8–11 and most preferred from 8–10.

Also useful as the nonionic surfactant of the surfactant systems of the present invention are alkylpolysaccharides disclosed in U.S. Pat. No. 4,565,647, having a hydrophobic group containing from about 6 to about 30 carbon atoms, preferably from about 10 to about 16 carbon atoms and a polysaccharide, e.g. a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties (optionally the hydrophobic group is attached at the 2-, 3-, 4-, etc. positions thus giving a glucose or galactose as opposed to a glucoside or galactoside). The intersaccharide bonds can be, e.g., between the one position of the additional saccharide units and the 2-, 3-, 4-, and/or 6-positions on the preceding saccharide units.

The preferred alkylpolyglycosides have the formula $$R^2O(C_nH_{2n}O)_t(\text{glycosyl})_x$$

wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, pre-ferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4-, and/or 6-position, preferably predominantly the 2-position.

The condensation products of ethylene oxide with a hydrophobic base formed by the condensation of propylene oxide with propylene glycol are also suitable for use as the additional nonionic surfactant systems of the present invention. The hydrophobic portion of these compounds will preferably have a molecular weight from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic™ surfactants, marketed by BASF.

Also suitable for use as the nonionic surfactant of the nonionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic™ compounds, marketed by BASF.

Preferred for use as the nonionic surfactant of the surfactant systems of the present invention are polyethylene oxide condensates of alkyl phenols, condensation products of primary and secondary aliphatic alcohols with from about 1 to about 25 moles of ethyleneoxide, alkylpolysaccharides, and mixtures hereof. Most preferred are $C_8$–$C_{14}$ alkyl phenol ethoxylates having from 3 to 15 ethoxy groups and $C_8$–$C_{18}$ alcohol ethoxylates (preferably $C_{10}$ avg.) having from 2 to 10 ethoxy groups, and mixtures thereof. Highly preferred nonionic surfactants are polyhydroxy fatty acid side surfactants of the formula

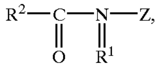

wherein $R^1$ is H, or $R^1$ is $C_{1-4}$ hydrocarbyl, 2-hydroxyethyl, 2-hydroxypropyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is straight $C_{11-15}$ alkyl or $C_{16-18}$ alkyl or alkenyl chain such as coconut alkyl or mixtures thereof, and Z is derived from a reducing sugar such as glucose, fructose, maltose or lactose, in a reductive amination reaction.

Highly preferred anionic surfactants include alkyl alkoxylated sulfate surfactants. Examples hereof are water soluble salts or acids of the formula $RO(A)_mSO3M$ wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydro-xyalkyl, more preferably $C_{12}$–$C_{18}$ alkyl or hydroxyalkyl, A is an ethoxy or propoxy unit, m is greater than zero, typically between about is 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl, trimethyl-ammonium cations and quaternary ammonium cations such as tetramethyl-ammonium and dimethyl piperdinium cations and those derived from alkylamines such as ethylamine, diethylamine, triethylamine, mixtures thereof, and the like. Exemplary surfactants are $C_{12}$–$C_{18}$ alkyl polyethoxylate (1.0) sulfate ($C_{12}$–$C_{18}$E(1.0)M), $C_{12}$–$C_{18}$ alkyl polyethoxylate (2.25) sulfate ($C_{12}$–$C_{18}$(2.25)M, and $C_{12}$–$C_{18}$ alkyl polyethoxylate (3.0) sulfate ($C_{12}$–$C_{18}$E(3.0)M), and $C_{12}$–$C_{18}$ alkyl polyethoxylate (4.0) sulfate ($C_{12}$–$C_{18}$E(4.0) M), wherein M is conveniently selected from sodium and potassium. Suitable anionic surfactants to be used are alkyl ester sulfonate surfactants including linear esters of $C_8$–$C_{20}$ carboxylic acids (i.e., fatty acids) which are sulfonated with gaseous $SO_3$ according to "The Journal of the American Oil Chemists Society", 52 (1975), pp. 323–329. Suitable starting materials would include natural fatty substances as derived from tallow, palm oil, etc.

The preferred alkyl ester sulfonate surfactant, especially for laundry applications, comprise alkyl ester sulfonate surfactants of the structural formula:

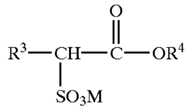

wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a cation which forms a water soluble salt with the alkyl ester sulfonate. Suitable salt-forming cations include metals such as sodium, potassium, and lithium, and substituted or unsubstituted ammonium cations, such as monoethanolamine, diethonolamine, and triethanolamine. Preferably, $R^3$ is $C_{10}$–$C_{16}$ alkyl, and $R^4$ is methyl, ethyl or isopropyl. Especially preferred are the methyl ester sulfonates wherein $R^3$ is $C_{10}$–$C_{16}$ alkyl.

Other suitable anionic surfactants include the alkyl sulfate surfactants which are water soluble salts or acids of the formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperdinium cations and quaternary ammonium cations derived from alkylamines such as ethylamine, diethylamine, triethylamine, and mixtures thereof, and the like). Typically, alkyl chains of $C_{12}$–$C_{16}$ are preferred for lower wash temperatures (e.g. below about 50° C.) and $C_{16}$–$C_{18}$ alkyl chains are preferred for higher wash temperatures (e.g. above about 50° C.).

Other anionic surfactants useful for detersive purposes can also be included in the laundry detergent compositions of the present invention. Theses can include salts (including, for example, sodium, potassium, ammonium, and substituted ammonium salts such as mono- di- and triethanolamine salts) of soap, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl glycerol sulfonates, fatty acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$–$C_{18}$ monoesters) and diesters of sulfosuccinates (especially saturated and unsaturated $C_6$–$C_{12}$ diesters), acyl sarcosinates, sulfates of alkylpolysaccharides such as the sulfates of alkylpolyglucoside (the nonionic nonsulfated compounds being described below), branched primary alkyl sulfates, and alkyl polyethoxy carboxylates such as those of the formula $RO(CH_2CH_2O)_k$—$CH_2C00$—M+ wherein R is a $C_8$–$C_{22}$ alkyl, k is an integer from 1 to 10, and M is a soluble salt forming cation. Resin acids and hydrogenated resin acids are also suitable, such as rosin, hydrogenated rosin, and resin acids and hydrogenated resin acids present in or derived from tall oil.

Alkylbenzene sulfonates are highly preferred. Especially preferred are linear (straight-chain) alkyl benzene sulfonates (LAS) wherein the alkyl group preferably contains from 10 to 18 carbon atoms.

Further examples are described in "Surface Active Agents and Detergents" (Vol. I and II by Schwartz, Perrry and Berch). A variety of such surfactants are also generally disclosed in U.S. Pat. No. 3,929,678, (Column 23, line 58 through Column 29, line 23, herein incorporated by reference).

When included therein, the laundry detergent compositions of the present invention typically comprise from about 1% to about 40%, preferably from about 3% to about 20% by weight of such anionic surfactants.

The laundry detergent compositions of the present invention may also contain cationic, ampholytic, zwitterionic, and semi-polar surfactants, as well as the nonionic and/or anionic surfactants other than those already described herein.

Cationic detersive surfactants suitable for use in the laundry detergent compositions of the present invention are those having one long-chain hydrocarbyl group. Examples of such cationic surfactants include the ammonium surfactants such as alkyltrimethylammonium halogenides, and those surfactants having the formula:

$$[R^2(OR^3)_y][R^4(OR^3)_y]_2R^5N+X-$$

wherein $R^2$ is an alkyl or alkyl benzyl group having from about 8 to about 18 carbon atoms in the alkyl chain, each $R^3$ is selected form the group consisting of —$CH_2CH_2$—, —$CH_2CH(CH_3)$—, —$CH_2CH(CH_2OH)$—, —$CH_2CH_2CH_2$—, and mixtures thereof; each $R^4$ is selected from the group consisting of $C_1$–$C_4$ alkyl, $C_1$–$C_4$ hydroxyalkyl, benzyl ring structures formed by joining the two $R^4$ groups, —$CH_2CHOHCHOHCOR^6CHOHCH_2OH$, wherein $R^6$ is any hexose or hexose polymer having a molecular weight less than about 1000, and hydrogen when y is not 0; $R^5$ is the same as $R^4$ or is an alkyl chain, wherein the total number of carbon atoms or $R^2$ plus $R^5$ is not more than about 18; each y is from 0 to about 10, and the sum of the y values is from 0 to about 15; and X is any compatible anion.

Highly preferred cationic surfactants are the water soluble quaternary ammonium compounds useful in the present composition having the formula:

$$R_1R_2R_3R_4N^+X^- \quad (i)$$

wherein $R_1$ is $C_8$–$C_{16}$ alkyl, each of $R_2$, $R_3$ and $R_4$ is independently $C_1$–$C_4$ alkyl, $C_1$–$C_4$ hydroxy alkyl, benzyl, and —$(C_2H_{40})_xH$ where x has a value from 2 to 5, and X is an anion. Not more than one of $R_2$, $R_3$ or $R_4$ should be benzyl.

The preferred alkyl chain length for $R_1$ is $C_{12}$–$C_{15}$, particularly where the alkyl group is a mixture of chain lengths derived from coconut or palm kernel fat or is derived synthetically by olefin build up or OXO alcohols synthesis.

Preferred groups for $R_2R_3$ and $R_4$ are methyl and hydroxyethyl groups and the anion X may be selected from halide, methosulphate, acetate and phosphate ions.

Examples of suitable quaternary ammonium compounds of formulae (i) for use herein are:

coconut trimethyl ammonium chloride or bromide;

coconut methyl dihydroxyethyl ammonium chloride or bromide;

decyl triethyl ammonium chloride;

decyl dimethyl hydroxyethyl ammonium chloride or bromide;

$C_{12-15}$ dimethyl hydroxyethyl ammonium chloride or bromide;

coconut dimethyl hydroxyethyl ammonium chloride or bromide;

myristyl trimethyl ammonium methyl sulphate;

lauryl dimethyl benzyl ammonium chloride or bromide;

lauryl dimethyl $(ethenoxy)_4$ ammonium chloride or bromide;

choline esters (compounds of formula (i) wherein $R_1$ is

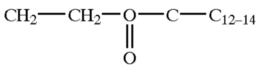

alkyl and $R_2R_3R_4$ are methyl).

di-alkyl imidazolines [compounds of formula (i)].

Other cationic surfactants useful herein are also described in U.S. Pat. No. 4,228,044 and in EP 000 224.

When included therein, the laundry detergent compositions of the present invention typically comprise from 0.2% to about 25%, preferably from about 1% to about 8% by weight of such cationic surfactants.

Ampholytic surfactants are also suitable for use in the laundry detergent compositions of the present invention. These surfactants can be broadly described as aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g. carboxy, sulfonate, sulfate. See U.S. Pat. No. 3,929,678 (column 19, lines 18–35) for examples of ampholytic surfactants.

When included therein, the laundry detergent compositions of the present invention typically comprise from 0.2% to about 15%, preferably from about 1% to about 10% by weight of such ampholytic surfactants.

Zwitterionic surfactants are also suitable for use in laundry detergent compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 (column 19, line 38 through column 22, line 48) for examples of zwitterionic surfactants.

When included therein, the laundry detergent compositions of the present invention typically comprise from 0.2% to about 15%, preferably from about 1% to about 10% by weight of such zwitterionic surfactants.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula:

O

-

$R^3(OR^4)xN(R^5)2$ wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3: and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides.

When included therein, the laundry detergent compositions of the present invention typically comprise from 0.2% to about 15%, preferably from about 1% to about 10% by weight of such semi-polar nonionic surfactants.

Builder System

The compositions according to the present invention may further comprise a builder system. Any conventional builder system is suitable for use herein including aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylenephosphonic acid. Though less preferred for obvious environmental reasons, phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Another suitable inorganic builder material is layered silicate, e.g. SKS-6 (Hoechst). SKS-6 is a crystalline layered silicate consisting of sodium silicate $(Na_2Si_2O_5)$.

Suitable polycarboxylates containing one carboxy group include lactic acid, glycolic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German offenle-enschrift 2,446,686, and 2,446,487, U.S. Pat. No.

3,935,257 and the sulfinyl carboxylates described in Belgian Patent No. 840,623. Polycarboxylates containing three carboxy groups include, in particular, -water-soluble citrates, aconitrates and citraconates. as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2, -ethane tetracarboxylates, 1,1,3,3-propane tetrac7arboxylates containing sulfo substituents include the sulfosuccinate derivatives disclosed in British Patent Nos. 1,398,421 and 1,398,422 and in U.S. Pat. No. 3,936,448, and the sulfonated pyrolysed citrates described in British Patent No. 1,082,179, while polycarboxylates containing phosphone substituents are disclosed in British Patent No. 1,439,000.

Alicyclic and heterocyclic polycarboxylates include cyclopentane-cis,cis-cis-tetracarboxylates, cyclopentadienide pentacarboxylates, 2,3,4,5-tetrahydro-furan-cis, cis, cis-tetracarboxylates, 2,5-tetrahydro-furan-cis, discarboxylates, 2,2,5,5, -tetrahydrofuran-tetracarboxylates, 1,2,3,4,5,6-hexane-hexacarboxylates and carboxymethyl derivatives of polyhydric alcohols such as sorbitol, mannitol and xylitol. Aromatic polycarboxylates include mellitic acid, pyromellitic acid and the phthalic acid derivatives disclosed in British Patent No. 1,425,343.

Of the above, the preferred polycarboxylates are hydroxycarboxylates containing up to three carboxy groups per molecule, more particularly citrates.

Preferred builder systems for use in the present compositions include a mixture of a water-insoluble aluminosilicate builder such as zeolite A or of a layered silicate (SKS-6), and a water-soluble carboxylate chelating agent such as citric acid.

A suitable chelant for inclusion in the detergent composiions in accordance with the invention is ethylenediamine-N,N'-disuccinic acid (EDDS) or the alkali metal, alkaline earth metal, ammonium, or substituted ammonium salts thereof, or mixtures thereof. Preferred EDDS compounds are the free acid form and the sodium or magnesium salt thereof; Examples of such preferred sodium salts of EDDS include $Na_2EDDS$ and $Na_4EDDS$. Examples of such preferred magnesium salts of EDDS include MgEDDS and $Mg_2EDDS$. The magnesium salts are the most preferred for inclusion in compositions in accordance with the invention.

Preferred builder systems include a mixture of a water-insoluble aluminosilicate builder such as zeolite A, and a water soluble carboxylate chelating agent such as citric acid.

Other builder materials that can form part of the builder system for use in granular compositions include inorganic materials such as alkali metal carbonates, bicarbonates, silicates, and organic materials such as the organic phosphonates, amino polyalkylene phosphonates and amino polycarboxylates.

Other suitable water-soluble organic salts are the homo- or co-polymeric acids or their salts, in which the polycarboxylic acid comprises at least two carboxyl radicals separated form each other by not more than two carbon atoms.

Polymers of this type are disclosed in GB-A-1,596,756. Examples of such salts are polyacrylates of MW 2000–5000 and their copolymers with maleic anhydride, such copolymers having a molecular weight of from 20,000 to 70,000, especially about 40,000.

Detergency builder salts are normally included in amounts of from 5% to 80% by weight of the composition. Preferred levels of builder for liquid detergents are from 5% to 30%.

Enzymes

Preferred detergent compositions, in addition to the enzyme preparation of the invention, comprise other enzyme (s) which provides cleaning performance and/or fabric care benefits.

Such enzymes include proteases, lipases, cutinases, amylases, cellulases, peroxidases, oxidases (e.g. laccases).

Proteases

Any protease suitable for use in alkaline solutions can be used. Suitable proteases include those of animal, vegetable or microbial origin. Microbial origin is preferred. Chemically or genetically modified mutants are included. The protease may be a serine protease, preferably an alkaline microbial protease or a trypsin-like protease. Examples of alkaline proteases are subtilisins, especially those derived from *Bacillus*, e.g., *subtilisin Novo, subtilisin Carlsberg, subtilisin* 309, *subtilisin* 147 and *subtilisin* 168 (described in WO 89/06279). Examples of trypsin-like proteases are trypsin (e.g. of porcine or bovine origin) and the Fusarium protease described in WO 89/06270.

Preferred commercially available protease enzymes include those sold under the trade names Alcalase, Savinase, Primase, Durazym, and Esperase by Novo Nordisk A/S (Denmark), those sold under the tradename Maxatase, Maxacal, Maxapem, Properase, Purafect and Purafect OXP by Genencor International, and those sold under the tradename Opticlean and Optimase by Solvay Enzymes. Protease enzymes may be incorporated into the compositions in accordance with the invention at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Lipases

Any lipase suitable for use in alkaline solutions can be used. Suitable lipases include those of bacterial or fungal origin. Chemically or genetically modified mutants are included.

Examples of useful lipases include a *Humicola lanuginosa* lipase, e.g., as described in EP 258 068 and EP 305 216, a *Rhizomucor miehei* lipase, e.g., as described in EP 238 023, a Candida lipase, such as a *C. antarctica* lipase, e.g., the *C. antarctica* lipase A or B described in EP 214 761, a Pseudomonas lipase such as a *P. alcaligenes* and *P. pseudoalcaligenes* lipase, e.g., as described in EP 218 272, a *P. ceparia* lipase, e.g., as described in EP 331 376, a *P. stutzeri* lipase, e.g., as disclosed in GB 1,372,034, a *P. fluorescens* lipase, a *Bacillus lipase*, e.g., a *B. subtilis* lipase (Dartois et al., (1993), Biochemica et Biophysica acta 1131, 253–260), a *B. steorothermophilus* lipase (JP 64/744992) and a *B. pumilus* lipase (WO 91/16422).

Furthermore, a number of cloned lipases may be useful, including the *Penicillium camembertii* lipase described by Yamaguchi et al., (1991), Gene 103, 61–67), the *Geotricum candidum* lipase (Schimada, Y. et al., (1989), J. Biochem., 106, 383–388), and various Rhizopus lipases such as a *R. delemar* lipase (Hass, M. J et al., (1991), Gene 109, 117–113), a *R. niveus* lipase (Kugimiya et al., (1992), Biosci. Biotech. Biochem. 56, 716–719) and a *R. oryzae* lipase.

Other types of lipolytic enzymes such as cutinases may also be useful, e.g., a cutinase derived from *Pseudomonas mendocina* as described in WO 88/09367, or a cutinase derived from *Fusarium solani pisi* (e.g. described in WO 90/09446).

Especially suitable lipases are lipases such as M1 Lipase™, Luma fast™ and Lipomax™ (Genencor), Lipolase™ and Lipolase Ultra™ (Novo Nordisk A/S), and Lipase P "Amano" (Amano Pharmaceutical Co. Ltd.).

The lipases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Amylases

Any amylase (a and/or b) suitable for use in alkaline solutions can be used. Suitable amylases include those of bacterial or fungal origin. Chemically or genetically modified mutants are included. Amylases include, for example, a-amylases obtained from a special strain of *B. lichemiformis*, described in more detail in GB 1,296,839. Commercially available amylases are Duramyl™, Termamyl™, Fungamyl™ and BAN™ (available from Novo Nordisk A/S) and Rapidase™ and Maxamyl P™ (available from Genencor).

The amylases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Cellulases

Any cellulase suitable for use in alkaline solutions can be used. Suitable cellulases include those of bacterial or fungal origin. Chemically or genetically modified mutants are included. Suitable cellulases are disclosed in U.S. Pat. No. 4,435,307 which discloses fungal cellulases produced from *Humicola insolens*, in WO 96/34108 and WO 96/34092 which disclose bacterial alkalophilic cellulases (BCE 103) from Bacillus, and in WO 94/21801, U.S. Pat. Nos. 5,475, 101 and 5,419,778 which disclose EG III cellulases from Trichoderma. Especially suitable cellulases are the cellulases having colour care benefits. Examples of such cellulases are cellulases described in European patent application No. 0 495 257. Commercially available cellulases include Celluzyme™ and Carezyme™ produced by a strain of *Humicola insolens* (Novo Nordisk A/S), KAC-500(B)™ (Kao Corporation), and Puradax™ (Genencor International).

Cellulases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Peroxidases/Oxidases

Peroxidase enzymes are used in combination with hydrogen peroxide or a source thereof (e.g. a percarbonate, perborate or persulfate). Oxidase enzymes are used in combination with oxygen. Both types of enzymes are used for "solution bleaching", i.e. to prevent transfer of a textile dye from a dyed fabric to another fabric when said fabrics are washed together in a wash liquor, preferably together with an enhancing agent as described in e.g. WO 94/12621 and WO 95/01426. Suitable peroxidases/oxidases include those of plant, bacterial or fungal origin. Chemically or genetically modified mutants are included.

Peroxidase and/or oxidase enzymes are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Mixtures of the above mentioned enzymes are encompassed herein, in particular a mixture of a protease, an amylase, a lipase and/or a cellulase.

The enzyme of the invention, or any other enzyme incorporated in the detergent composition, is normally incorporated in the detergent composition at a level from 0.00001% to 2% of enzyme protein by weight of the composition, preferably at a level from 0.0001% to 1% of enzyme protein by weight of the composition, more preferably at a level from 0.001% to 0.5% of enzyme protein by weight of the composition, even more preferably at a level from 0.01% to 0.2% of enzyme protein by weight of the composition.

Bleaching Agents

Additional optional detergent ingredients that can be included in the detergent compositions of the present invention include bleaching agents such as PB1, PB4 and percarbonate with a particle size of 400–800 microns. These bleaching agent components can include one or more oxygen bleaching agents and, depending upon the bleaching agent chosen, one or more bleach activators. When present oxygen bleaching compounds will typically be present at levels of from about 1% to about 25%. In general, bleaching compounds are optional added components in non-liquid formulations, e.g. granular detergents.

The bleaching agent component for use herein can be any of the bleaching agents useful for detergent compositions including oxygen bleaches as well as others known in the art.

The bleaching agent suitable for the present invention can be an activated or non-activated bleaching agent.

One category of oxygen bleaching agent that can be used encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching agents are disclosed in U.S. Pat. Nos. 4,483,781, 740,446, EP 0 133 354 and U.S. Pat. No. 4,412, 934. Highly preferred bleaching agents also include 6-nonylamino-6-oxoperoxycaproic acid as described in U.S. Pat. No. 4,634,551.

Another category of bleaching agents that can be used encompasses the halogen bleaching agents. Examples of hypohalite bleaching agents, for example, include trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

The hydrogen peroxide releasing agents can be used in combination with bleach activators such as tetraacetylethylenediamine (TAED), nonanoyloxybenzenesulfonate (NOBS, described in U.S. Pat. No. 4,412,934), 3,5-trimethylhexsanoloxybenzenesulfonate (ISONOBS, described in EP 120 591) or pentaacetylglucose (PAG), which are perhydrolyzed to form a peracid as the active bleaching species, leading to improved bleaching effect. In addition, very suitable are the bleach activators C8(6-octanamido-caproyl) oxybenzene-sulfonate, C9(6-nonanamido caproyl) oxybenzenesulfonate and C10 (6-decanamido caproyl) oxybenzenesulfonate or mixtures thereof. Also suitable activators are acylated citrate esters such as disclosed in European Patent Application No. 91870207.7.

Useful bleaching agents, including peroxyacids and bleaching systems comprising bleach activators and peroxygen bleaching compounds for use in cleaning compositions according to the invention are described in application U.S. Ser. No. 08/136,626.

The hydrogen peroxide may also be present by adding an enzymatic system (i.e. an enzyme and-a substrate therefore) which is capable of generation of hydrogen peroxide at the beginning or during the washing and/or rinsing process. Such enzymatic systems are disclosed in European Patent Application EP 0 537 381.

Bleaching agents other than oxygen bleaching agents are also known in the art and can be utilized herein. One type of non-oxygen bleaching agent of particular interest includes photoactivated bleaching agents such as the sulfonated zinc and/or aluminium phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalocyanine and a photoactivated bleaching process are described in U.S. Pat. No. 4,033,718. Typically, detergent composition will contain about 0.025% to about 1.25%, by weight, of sulfonated zinc phthalocyanine.

Bleaching agents may also comprise a manganese catalyst. The manganese catalyst may, e.g., be one of the compounds described in "Efficient manganese catalysts for low-temperature bleaching", *Nature* 369, 1994, pp. 637–639.

Suds Suppressors

Another optional ingredient is a suds suppressor, exemplified by silicones, and silica-silicone mixtures. Silicones can generally be represented by alkylated polysiloxane materials, while silica is normally used in finely divided forms exemplified by silica aerogels and xerogels and hydrophobic silicas of various types. Theses materials can be incorporated as particulates, in which the suds suppressor is advantageously releasably incorporated in a water-soluble or waterdispersible, substantially non surface-active detergent impermeable carrier. Alternatively the suds suppressor can be dissolved or dispersed in a liquid carrier and applied by spraying on to one or more of the other components.

A preferred silicone suds controlling agent is disclosed in U.S. Pat. No. 3,933,672. Other particularly useful suds suppressors are the self-emulsifying silicone suds suppressors, described in German Patent Application DTOS 2,646,126. An example of such a compound is DC-544, commercially available form Dow Corning, which is a siloxane-glycol copolymer. Especially preferred suds controlling agent are the suds suppressor system comprising a mixture of silicone oils and 2-alkyl-alkanols. Suitable 2-alkyl-alkanols are 2-butyl-octanol which are commercially available under the trade name Isofol 12 R.

Such suds suppressor system are described in European Patent Application EP 0 593 841.

Especially preferred silicone suds controlling agents are described in European Patent Application No. 92201649.8. Said compositions can comprise a silicone/silica mixture in combination with fumed nonporous silica such as Aerosil®.

The suds suppressors described above are normally employed at levels of from 0.001% to 2% by weight of the composition, preferably from 0.01% to 1% by weight.

Other Components

Other components used in detergent compositions may be employed such as soil-suspending agents, soil-releasing agents, optical brighteners, abrasives, bactericides, tarnish inhibitors, coloring agents, and/or encapsulated or nonencapsulated perfumes.

Especially suitable encapsulating materials are water soluble capsules which consist of a matrix of polysaccharide and polyhydroxy compounds such as described in GB 1,464,616.

Other suitable water soluble encapsulating materials comprise dextrins derived from ungelatinized starch acid esters of substituted dicarboxylic acids such as described in U.S. Pat. No. 3,455,838. These acid-ester dextrins are, preferably, prepared from such starches as waxy maize, waxy sorghum, sago, tapioca and potato. Suitable examples of said encapsulation materials include N-Lok manufactured by National Starch. The N-Lok encapsulating material consists of a modified maize starch and glucose. The starch is modified by adding monofunctional substituted groups such as octenyl succinic acid anhydride.

Antiredeposition and soil suspension agents suitable herein include cellulose derivatives such as methylcellulose, carboxymethylcellulose and hydroxyethylcellulose, and homo- or co-polymeric polycarboxylic acids or-their salts. Polymers of this type include the polyacrylates and maleic anhydride-acrylic acid copolymers previously mentioned as builders, as well as copolymers of maleic anhydride with ethylene, methylvinyl ether or methacrylic acid, the maleic anhydride constituting at least 20 mole percent of the copolymer. These materials are normally used at levels of from 0.5% to 10% by weight, more preferably form 0.75% to 8%, most preferably from 1% to 6% by weight of the composition.

Preferred optical brighteners are anionic in character, examples of which are disodium 4,4'-bis-(2-diethanolamino-4-anilino-s-triazin-6-ylamino)stilbene-2:2'disulphonate, disodium 4,-4'-bis-(2-morpholino-4-anilino-s-triazin-6-ylamino-stilbene-2:2'-disulphonate, disodium 4,4'-bis-(2,4-dianilino-s-triazin-6-ylamino)stilbene-2:2'-disulphonate, monosodium 4', 4"-bis-(2,4-dianilino-s-tri-azin-6 ylamino) stilbene-2-sulphonate, disodium 4,4'-bis-(2-anilino-4-(N-methyl-N-2-hydroxyethylamino)-s-triazin-6-ylamino) stilbene-2,2'-disulphonate, di-sodium 4,4'-bis-(4-phenyl-2,1,3-triazol-2-yl)-stilbene-2,2'disulphonate, di-so-dium 4,4'bis(2-anilino-4-(1-methyl-2-hydroxyethylamino)-s-triazin-6-ylamino)stilbene-2,2'disulphonate, sodium 2(stilbyl-4"-(naphtho-1',2':4,5)-1,2,3,-triazole-2"-sulphonate and 4,4'-bis(2-sulphostyryl)biphenyl.

Other useful polymeric materials are the polyethylene glycols, particularly those of molecular weight 1000–10000, more particularly 2000 to 8000 and most preferably about 4000. These are used at levels of from 0.20% to 5% more preferably from 0.25% to 2.5% by weight. These polymers and the previously mentioned homo- or co-polymeric polycarboxylate salts are valuable for improving whiteness maintenance, fabric ash deposition, and cleaning performance on clay, proteinaceous and oxidizable soils in the presence of transition metal impurities.

Soil release agents useful in compositions of the present invention are conventionally copolymers or terpolymers of terephthalic acid with ethylene glycol and/or propylene glycol units in various arrangements. Examples of such polymers are disclosed in U.S. Pat. Nos. 4,116,885 and 4,711,730 and EP 0 272 033. A particular preferred polymer in accordance with EP 0 272 033 has the formula:

$$(CH_3\ (PEG)_{43})_{0.75}(POH)_{0.25}[T\text{-}PO)_{2.8}(T\text{-}PEG)_{0.4}]\ T(POH)_{0.25}((PEG)_{43}CH_3)_{0.75}$$

where PEG is —$(OC_2H_4)O$—, PO is $(OC_3H_6O)$ and T is $(pOOC_6H_4CO)$.

Also very useful are modified polyesters as random copolymers of dimethyl terephthalate, dimethyl sulfoisophthalate, ethylene glycol and 1,2-propanediol, the end groups consisting primarily of sulphobenzoate and secondarily of mono esters of ethylene glycol and/or 1,2-propanediol. The target is to obtain a polymer capped at both end by sulphobenzoate groups, "primarily", in the present context most of said copolymers herein will be endcapped by sulphobenzoate groups. However, some copolymers will be less than fully capped, and therefore their end groups may consist of monoester of ethylene glycol and/or 1,2-propanediol, thereof consist "secondarily" of such species.

The selected polyesters herein contain about 46% by weight of dimethyl terephthalic acid, about 16% by weight of 1,2-propanediol, about 10% by weight ethylene glycol, about 13% by weight of dimethyl sulfobenzoic acid and about 15% by weight of sulfoisophthalic acid, and have a molecular weight of about 3.000. The polyesters and their method of preparation are described in detail in EP 311 342.

Softening Agents

Fabric softening agents can also be incorporated into laundry detergent compositions in accordance with the present invention. These agents may be inorganic or organic in type. Inorganic softening agents are exemplified by the smectite clays disclosed in GB-A-1 400898 and in U.S. Pat. No. 5,019,292. Organic fabric softening agents include the water insoluble tertiary amines as disclosed in GB-A1 514 276 and EP 0 011 340 and their combination with mono $C_{12}$–$C_{14}$ quaternary ammonium salts are disclosed in EP-B-0 026 528 and di-long-chain amides as disclosed in EP 0 242 919. Other useful organic ingredients of fabric softening systems include high molecular weight polyethylene oxide materials as disclosed in EP 0 299 575 and 0 313 146.

Levels of smectite clay are normally in the range from 5% to 15%, more preferably from 8% to 12% by weight, with the material being added as a dry mixed component to the remainder of the formulation. Organic fabric softening agents such as the water-insoluble tertiary amines or dilong chain amide materials are incorporated at levels of from 0.5% to 5% by weight, normally from 1% to 3% by weight whilst the high molecular weight polyethylene oxide materials and the water soluble cationic materials are added at levels of from 0.1% to 2%, normally from 0.15% to 1.5% by weight. These materials are normally added to the spray dried portion of the composition, although in some instances it may be more convenient to add them as a dry mixed particulate, or spray them as molten liquid on to other solid components of the composition.

Polymeric Dye-transfer Inhibiting Agents

The detergent compositions according to the present invention may also comprise from 0.001% to 10%, preferably from 0.01% to 2%, more preferably form 0.05% to 1% by weight of polymeric dye-transfer inhibiting agents. Said polymeric dye-transfer inhibiting agents are normally incorporated into detergent compositions in order to inhibit the transfer of dyes from colored fabrics onto fabrics washed therewith. These polymers have the ability of complexing or adsorbing the fugitive dyes washed out of dyed fabrics before the dyes have the opportunity to become attached to other articles in the wash.

Especially suitable polymeric dye-transfer inhibiting agents are polyamine N-oxide polymers, copolymers of N-vinylpyrrolidone and N-vinylimidazole, polyvinylpyrrolidone polymers, polyvinyloxazolidones and polyvinylimidazoles or mixtures thereof.

Addition of such polymers also enhances the performance of the enzymes according the invention.

The detergent composition according to the invention can be in liquid, paste, gels, bars or granular forms.

Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

Granular compositions according to the present invention can also be in "compact form", i.e. they may have a relatively higher density than conventional granular detergents, i.e. form 550 to 950 g/l; in such case, the granular detergent compositions according to the present invention will contain a lower amount of "Inorganic filler salt", compared to conventional granular detergents; typical filler salts are alkaline earth metal salts of sulphates and chlorides, typically sodium sulphate; "Compact" detergent typically comprise not more than 10% filler salt. The liquid compositions according to the present invention can also be in "concentrated form", in such case, the liquid detergent compositions according to the present invention will contain a lower amount of water, compared to conventional liquid detergents. Typically, the water content of the concentrated liquid detergent is less than 30%, more preferably less than 20%, most preferably less than 10% by weight of the detergent compositions.

The compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

The following examples are meant to exemplify compositions for the present invention, but are not necessarily meant to limit or otherwise define the scope of the invention. In the detergent compositions, the abbreviated component identifications have the following meanings:

LAS: Sodium linear $C_{12}$ alkyl benzene sulphonate

TAS: Sodium tallow alkyl sulphate

XYAS: Sodium $C_{1X}$–$C_{1Y}$ alkyl sulfate

SS: Secondary soap surfactant of formula 2-butyl octanoic acid

25EY: A $C_{12}$–$C_{15}$ predominantly linear primary alcohol condensed with an average of Y moles of ethylene oxide 45EY: A $C_{14}$–$C_{15}$ predominantly linear primary alcohol condensed with an average of Y moles of ethylene oxide XYEZS: $C_{1X}$–$C_{1Y}$ sodium alkyl sulfate condensed with an average of Z moles of ethylene oxide per mole Nonionic: $C_{13}$–$C_{15}$ mixed ethoxylated/propoxylated fatty alcohol with an average degree of ethoxylation of 3.8 and an average degree of propoxylation of 4.5 sold under the tradename Plurafax LF404 by BASF Gmbh CFAA: $C_{12}$–$C_{14}$ alkyl N-methyl glucamide
TFAA: $C_{16}$–$C_{18}$ alkyl N-methyl glucamide
Silicate: Amorphous Sodium Silicate ($SiO_2$:$Na_2O$ ratio=2.0)
NaSKS-6: Crystalline layered silicate of formula d-$Na_2Si_2O_5$
Carbonate: Anhydrous sodium carbonate
Phosphate: Sodium tripolyphosphate
MA/AA: Copolymer of 1:4 maleic/acrylic acid, average molecular weight about 80,000
Polyacrylate: Polyacrylate homopolymer with an average molecular weight of 8,000 sold under the tradename PA30 by BASF GmbH
Zeolite A:. Hydrated Sodium Aluminosilicate of formula $Na_{12}(AlO_2SiO_2)_{12}$. $27H_2O$ having a primary particle size in the range from 1 to 10 micrometers
Citrate: Tri-sodium citrate dihydrate
Citric: Citric Acid
Perborate: Anhydrous sodium perborate monohydrate bleach, empirical formula $NaBO_2.H_2O_2$
PB4: Anhydrous sodium perborate tetrahydrate
Percarbonate: Anhydrous sodium percarbonate bleach of empirical formula $2Na_2CO_3.3H_2O_2$
TAED: Tetraacetyl ethylene diamine
CMC: Sodium carboxymethyl cellulose
DETPMP: Diethylene triamine penta (methylene phosphonic acid), marketed by Monsanto under the Tradename Dequest 2060
PVP: Polyvinylpyrrolidone polymer
EDDS: Ethylenediamine-N,N'-disuccinic acid, [S,S] isomer in the form of the sodium salt
Suds Suppressor: 25% paraffin wax Mpt 50° C., 17% hydrophobic silica, 58% paraffin oil
Granular Suds suppressor: 12% Silicone/silica, 18% stearyl alcohol, 70% starch in granular form
Sulphate: Anhydrous sodium sulphate
HMWPEO: High molecular weight polyethylene oxide
TAE 25: Tallow alcohol ethoxylate (25)

Detergent Example I

A granular fabric cleaning composition in accordance with the invention may be prepared as follows:

| | |
|---|---|
| Sodium linear $C_{12}$ alkyl benzene sulfonate | 6.5 |
| Sodium sulfate | 15.0 |
| Zeolite A | 26.0 |
| Sodium nitrilotriacetate | 5.0 |
| Enzyme of the invention | 0.1 |
| PVP | 0.5 |
| TAED | 3.0 |
| Boric acid | 4.0 |
| Perborate | 18.0 |
| Phenol sulphonate | 0.1 |
| Minors | Up to 100 |

Detergent Example II

A compact granular fabric cleaning composition (density 800 g/l) in accord with the invention may be prepared as follows:

| | |
|---|---|
| 45AS | 8.0 |
| 25E3S | 2.0 |
| 25E5 | 3.0 |

-continued

| | |
|---|---|
| 25E3 | 3.0 |
| TFAA | 2.5 |
| Zeolite A | 17.0 |
| NaSKS-6 | 12.0 |
| Citric acid | 3.0 |
| Carbonate | 7.0 |
| MA/AA | 5.0 |
| CMC | 0.4 |
| Enzyme of the invention | 0.1 |
| TAED | 6.0 |
| Percarbonate | 22.0 |
| EDDS | 0.3 |
| Granular suds suppressor | 3.5 |
| water/minors | Up to 100% |

Detergent Example III

Granular fabric cleaning compositions in accordance with the invention which are especially useful in the laundering of coloured fabrics were prepared as follows:

| | | |
|---|---|---|
| LAS | 10.7 | — |
| TAS | 2.4 | — |
| TFAA | — | 4.0 |
| 45AS | 3.1 | 10.0 |
| 45E7 | 4.0 | — |
| 25E3S | — | 3.0 |
| 68E11 | 1.8 | — |
| 25E5 | — | 8.0 |
| Citrate | 15.0 | 7.0 |
| Carbonate | — | 10 |
| Citric acid | 2.5 | 3.0 |
| Zeolite A | 32.1 | 25.0 |
| Na-SKS-6 | — | 9.0 |
| MA/AA | 5.0 | 5.0 |
| DETPMP | 0.2 | 0.8 |
| Enzyme of the invention | 0.10 | 0.05 |
| Silicate | 2.5 | — |
| Sulphate | 5.2 | 3.0 |
| PVP | 0.5 | — |
| Poly (4-vinylpyridine)-N-Oxide/copolymer of vinyl-imidazole and vinyl-pyrrolidone | — | 0.2 |
| Perborate | 1.0 | — |
| Phenol sulfonate | 0.2 | — |
| Water/Minors | Up to 100% | |

Detergent Example IV

Granular fabric cleaning compositions in accordance with the invention which provide "Softening through the wash" capability may be prepared as follows:

| | | |
|---|---|---|
| 45AS | — | 10.0 |
| LAS | 7.6 | — |
| 68AS | 1.3 | — |
| 45E7 | 4.0 | — |
| 25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| Perborate | 15.0 | — |
| Percarbonate | — | 15.0 |

-continued

| | | |
|---|---|---|
| TAED | 5.0 | 5.0 |
| Smectite clay | 10.0 | 10.0 |
| HMWPEO | — | 0.1 |
| Enzyme of the invention | 0.10 | 0.05 |
| Silicate | 3.0 | 5.0 |
| Carbonate | 10.0 | 10.0 |
| Granular suds suppressor | 1.0 | 4.0 |
| CMC | 0.2 | 0.1 |
| Water/Minors | Up to 100% | |

Detergent Example V

Heavy duty liquid fabric cleaning compositions in accordance with the invention may be prepared as follows:

| | I | II |
|---|---|---|
| LAS acid form | — | 25.0 |
| Citric acid | 5.0 | 2.0 |
| 25AS acid form | 8.0 | — |
| 25AE2S acid form | 3.0 | — |
| 25AE7 | 8.0 | — |
| CFAA | 5 | — |
| DETPMP | 1.0 | 1.0 |
| Fatty acid | 8 | — |
| Oleic acid | — | 1.0 |
| Ethanol | 4.0 | 6.0 |
| Propanediol | 2.0 | 6.0 |
| Enzyme of the invention | 0.10 | 0.05 |
| Coco-alkyl dimethyl hydroxy ethyl ammonium chloride | — | 3.0 |
| Smectite clay | — | 5.0 |
| PVP | 2.0 | — |
| Water/Minors | Up to 100% | |

Use in the Textile and Cellulosic Fiber Processing Industries

In the present context, the term "cellulosic material" is intended to mean fibers, sewn and unsewn fabrics, including knits, wovens, denims, yarns, and toweling, made from cotton, cotton blends or natural or manmade cellulosics (e.g. originating from xylan-containing cellulose fibers such as from wood pulp) or blends thereof. Examples of blends are blends of cotton or rayon/viscose with one or more companion material such as wool, synthetic fibers (e.g. polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g. rayon/viscose, ramie, hemp, flax/linen, jute, cellulose acetate fibers, lyocell).

The preparation of the present invention is useful in the cellulosic fiber processing industry for the pretreatment or retting of fibers from hemp, flax or linen.

The processing of cellulosic material for the textile industry, as for example cotton fiber, into a material ready for garment manufacture involves several steps: spinning of the fiber into a yarn; construction of woven or knit fabric from the yarn and subsequent preparation, dyeing and finishing operations. Woven goods are constructed by weaving a filling yarn between a series of warp yarns; the yarns could be two different types. Knitted goods are constructed by forming a network of interlocking loops from one continuous length of yarn. The cellulosic fibers can also be used for non-woven fabric.

The preparation process prepares the textile for the proper response in dyeing operations. The sub-steps involved in preparation are desizing (for woven goods), scouring and bleaching. A one step combined scour/bleach process is also used by the industry. Although preparation processes are most commonly employed in the fabric state; scouring, bleaching and dyeing operations can also be done at the fiber or yarn stage.

The processing regime can be either batch or continuous with the fabric being contacted by the liquid processing stream in open width or rope form. Continuous operations generally use a saturator whereby an approximate equal weight of chemical bath per weight of fabric is applied to the fabric, followed by a heated dwell chamber where the chemical reaction takes place. A washing section then prepares the fabric for the next processing step. Batch processing generally takes place in one processing bath whereby the fabric is contacted with approximately 8–15 times its weight in chemical bath. After a reaction period, the chemicals are drained, fabric rinsed and the next chemical is applied. Discontinuous pad-batch processing involves a saturator whereby an approximate equal weight of chemical bath per weight of fabric is applied to the fabric, followed by a dwell period which in the case of cold pad-batch might be one or more days.

Woven goods are the prevalent form of textile fabric construction. The weaving process demands a "sizing" of the warp yarn to protect it from abrasion. Starch, polyvinyl alcohol (PVA), carboxymethyl cellulose, waxes and acrylic binders are examples of typical sizing chemicals used because of availability and cost. The size must be removed after the weaving process as the first step in preparing the woven goods. The sized fabric in either rope or open width form is brought in contact with the processing liquid containing the desizing agents. The desizing agent employed depends upon the type of size to be removed. For PVA sizes, hot water or oxidative processes are often used. The most common sizing agent for cotton fabric is based upon starch. Therefore most often, woven cotton fabrics are desized by a combination of hot water, the enzyme α-amylase to hydrolyze the starch and a wetting agent or surfactant. The cellulosic material is allowed to stand with the desizing chemicals for a "holding period" sufficiently long to accomplish the desizing. The holding period is dependent upon the type of processing regime and the temperature and can vary from 15 minutes to 2 hours, or in some cases, several days. Typically, the desizing chemicals are applied in a saturator bath which generally ranges from about 15° C. to about 55° C. The fabric is then held in equipment such as a "J-box" which provides sufficient heat, usually between about 55° C. and about 100° C., to enhance the activity of the desizing agents. The chemicals, including the removed sizing agents, are washed away from the fabric after the termination of the holding period.

In order to ensure a high whiteness or a good wettability and resulting dyeability, the size chemicals and other applied chemicals must be thoroughly removed. It is generally believed that an efficient desizing is of crucial importance to the following preparation processes: scouring and bleaching.

The scouring process removes much of the non-cellulosic compounds naturally found in cotton. In addition to the natural non-cellulosic impurities, scouring can remove dirt, soils and residual manufacturing introduced materials such as spinning, coning or slashing lubricants. The scouring process employs sodium hydroxide or related causticizing agents such as sodium carbonate, potassium hydroxide or mixtures thereof. Generally an alkali stable surfactant is added to the process to enhance solubilization of hydrophobic compounds and/or prevent their redeposition back on the fabric. The treatment is generally at a high temperature, 80°

C.–100° C., employing strongly alkaline solutions, pH 13–14, of the scouring agent. Due to the non-specific nature of chemical processes not only are the impurities but the cellulose itself is attacked, leading to damages in strength or other desirable fabric properties. The softness of the cellulosic fabric is a function of residual natural cotton waxes. The non-specific nature of the high temperature strongly alkaline scouring process cannot discriminate between the desirable natural cotton lubricants and the manufacturing introduced lubricants. Furthermore, the conventional scouring process can cause environmental problems due to the highly alkaline effluent from these processes. The scouring stage prepares the fabric for the optimal response in bleaching. An inadequately scoured fabric will need a higher level of bleach chemical in the subsequent bleaching stages.

The bleaching step decolorizes the natural cotton pigments and removes any residual natural woody cotton trash components not completely removed during ginning, carding or scouring. The main process in use today is an alkaline hydrogen peroxide bleach. In many cases, especially when a very high whiteness is not needed, bleaching can be combined with scouring.

It is contemplated that the scouring step can be carried out using the xyloglucanase or xyloglucanase preparation of the present invention in combination with a few other enzyme activities at a temperature of about 50° C.–80° C. and a pH of about 7–11, thus substituting or supplementing the highly causticizing agents.

MATERIALS AND METHODS

Fungal Strains

*Malbranchea cinnamomea*, CBS960.72

*Malbranchea cinnamomea*, CBS343.55

*Malbranchea cinnamomea*, UAMH2485.

These strains are all publicly available strains from recognized culture collections:

CBS
Centraalbureau voor Schimmelcultures
Oosterstraat 1
Postbus 273
NL-3740 AG Baarn
Netherlands UAMH
University of Alberta Microfungus Collection & Herbarium
Devonian Botanic Garden
Edmonton, AB, Canada T6G 2E1

Media

YG: Yeast-glucose Agar 5.0 g Difco powdered yeast extract; 10.0 g glucose; 20.0 g agar; 1000 ml tap water. Autoclave at 121° C. for 15–20 min.

Media A Per Flask 30 g wheat bran; 45 ml of the following solution: 4 g Yeast Extract, 1 g $KH_2PO_4$, 0.5 g $MgSO_47H_2O$, 15 g Glucose; 1000 ml Tap water. Autoclave at 121° C. for 30 min.

Media B (50 ml/flask)

30 g Soymeal; 15 g Maltose; 5 g Peptone; 1000 ml $H_2O$; 1 g olive oil (2 drops/flask). 50 ml in 500 ml Erlenmeyer flask with 2 baffles. Autoclave at 121° C. for 30 min.

Fermentation Procedure

The fungal strains were grown on YG agar plate (4.5 cm diameter) for 3 days under 45° C. in the darkness and used for inoculating shake flask. The plates with fully grown cultures were stored at 4° C. before use.

For enzyme production, 4–6 agar plugs with fully grown fungal cultures on the above plates were used to inoculate one shake flask with media B and grown under 45° C., 160 rpm for 12–24 hours and used for inoculating shake flask with media A in order to obtain enough culture broth.

About 1 ml above cultivated culture broth was used to inoculate each flask with media A. The inoculated flasks were grown for 4 days under 45° C. and stationary conditions.

Sample Preparation for Enzyme Activity Test and Purification

To each flask with wheat bran and fully grown culture in media A was added 150 ml tap water and homogenized by a sterilized glass rod. The enzyme extraction was extracted by leaving the flask at 4° C. for 2 hours. The culture broth was then centrifuged at 8000 rpm and 4° C. for 30 minutes and the supernatant was collected and tested for cellulase, β-glucanase and xyloglucanase activity.

Enzyme Activity Tests

Agarose Plate Assay

Agarose plates containing 1% agarose in phosphate-citrate buffer pH 3, pH 7 and pH 10, 0.1% AZCL-xyloglucan, 0.1% AZCL-HE-cellulose and 0.1% AZCL-β-glucan (Megazyme, Australia), respectively; 20 μl sample was applied into d=4 mm holes in the agarose plates, incubation at 45° C. for 12–16 hours. Enzyme activity was identified by blue halos.

Microtiter Plate Assay

A solution of 0.2% of the blue substrate AZCL-substrate (AZCL-xyloglucan, AZCL-HE-cellulose, AZCL-β-glucan) is suspended in a 0.1 M phosphate-citrate buffer (pH 3–6) or Borax/$NaH_2PO_4$ buffer (pH 7–9) or glycine buffer (pH 9–11) under stirring. The solution is distributed under stirring to microtiter plate (80 μl to each well), 20 μm enzyme sample is added and they are incubated in a Eppendorf Thermomixer for 1 hour at 50° C. and 800 rpm. Denatured enzyme sample (100° C. boiling for 20 min) was used as blank. After incubation the coloured solution is separated from the solid by centrifugation at 3000 rpm for 5 minutes at 4° C. 60 μl of supernatant was transferred into a microtiter plate and the absorbance is measured by BioRad Microplate Reader at 595 nm.

Eppendorf Tube Assay

A solution of 0.2% of the blue substrate AZCL-substrate (AZCL-xyloglucan, AZCL-HE-cellulose, AZCL-β-glucan) is suspended in a 0.1 M phosphate-citrate buffer (pH 3–6) or Borax/$NaH_2PO_4$ buffer (pH 7–9) or glycine buffer (pH 9–11) under stirring. The solution is distributed under stirring to 1.5 ml Eppendorf tubes (900 μl to each), 100 μm enzyme sample is added and they are incubated in a water bath for 10–60 min. at 50° C. Denatured enzyme sample (100° C. boiling for 20 min) was used as blank. After incubation the coloured solution is separated from the solid by centrifugation at 5000 rpm for 10 minutes at 4° C. 200 μl of supernatant was transferred into a microtiter plate and the absorbency is measured by BioRad Microplate Reader at 595 nm.

Isoelectric Focusing

Isoelectric focusing was carried out in precast Ampholine PAG plates pH 3.5–9.5 (Pharmacia, Sweden) according to the manufacturer's instructions. The samples were applied in triplicate and after electrophoresis the gel was divided into three. An overlay containing 1% agarose and 0.4% AZCL-xyloglucan, or 0.4% AZCL-HE-cellulose, or 0.4% AZCL-β-1,4-glucan in buffer pH 9 was poured onto each part of gel. Incubation at 45° C. for 12–16 hours. Enzyme activity and pI of enzyme protein as identified by blue zones.

General Molecular Biology Methods

Unless otherwise stated all the DNA manipulations and transformations were performed using standard methods of molecular biology (Sambrook et al. (1989) Molecular clon
ing: A laboratory manual, Cold Spring Harbor lab., Cold Spring Harbor, NY; Ausubel, F. M. et al. (eds.) "Current protocols in Molecular Biology". John Wiley and Sons, 1995. Enzymes for DNA manipulations were used according to the manufacturer's instructions (e.g. restriction endonucleases, ligases etc. are obtainable from New England Biolabs, Inc.).

Plasmids pYES 2.0 (Invitrogen, USA)

pMT2188

Construction of the Expression Plasmid pMT 2188

The *Aspergillus oryzae* expression plasmid pCaHj 483 (WO 98/00529) consist of an expression cassette based on the *Aspergillus niger* neutral amylase II promoter fused to the *Aspergillus nidulans* triose phosphate isomerase non translated leader sequence (Pna2/tpi) and the *Aspergillus niger* amyloglycosidase terminater (Tamg). Also present on the plasmid is the Aspergillus selective marker amdS from *Aspergillus nidulans* enabling growth on acetamide as sole nitrogen source. These elements are cloned into the *E. coli* vector pUC19. The ampecillin resistance marker enabling selection in *E. coli* of this plasmid was replaced with the URA3 marker of *Saccharomyces cerevisiae* that can complement a pyrF mutation in *E. coli* in the following way:

The pUC19 origin of replication was PCR amplified from pCaHj483 with the primers:

142779: TTG AAT TGA AAA TAG ATT GAT TTA AAA CTT C (SEQ ID NO:3)

142780: TTG CAT GCG TAA TCA TGG TCA T AG C (SEQ ID NO:4)

The primer 142780 introduces a Bbu I site in the PCR fragment.

The Expand PCR system (Roche Molecular Biochemicals, Basel, Switserland) was used for the amplification following the manufacturers instructions for this and the subsequent PCR amplifications.

The URA3 gene was amplified from the general *S. cerevisiae* cloning vector pYES2 (Invitrogen corporation, Carlsbad, Calif., USA) using the primers:

140288: TTG AAT TCA TGG GTA ATA ACT G AT AT (SEQ ID NO:5)

142778: AAA TCA ATC TAT TTT CAA TTC AAT TCA TCA TT (SEQ ID NO:6)

The primer 140288 introduces an EcoR I site in the PCR fragment.

The two PCR fragments were fused by mixing them and amplifying using the primers 142780 and 140288 using the splicing by overlap method (Horton et al (1989) Gene, 77, 61–68).

The resulting fragment was digested with EcoR I and Bbu I and ligated to the largest fragment of pCaHj 483 digested with the same enzymes. The ligation mixture was used to transform the pyrF$^-$ *E. coli* strain DB6507 (ATCC 35673) made competent by the method of Mandel and Higa (Mandel, M. and A. Higa (1970) J. Mol. Biol. 45, 154). Transformants were selected on solid M9 medium (Sambrook et. al (1989) Molecular cloning, a laboratory manual, 2. edition, Cold Spring Harbor Laboratory Press) supplemented with 1 g/l casaminoacids, 500 $\mu$g/l thiamine and 10 mg/l kanamycin.

A plasmid from such a transformant was termed pCaHj 527. The construction of the plasmid is outlined in figure xxx. ThePna2/tpi promoter present on pCaHj527 was subjected to site directed mutagenises by a simple PCR approach.

Nucleotide 134–144 was altered from GTACTAAAACC (SEQ ID NO:7) to CCGTTAAATTT (SEQ ID NO:8) using the mutagenic primer 141223:

141223 GGA TGC TGT TGA CTC CGG AAA TTT AAC GGT TTG GTC TTG CAT CCC (SEQ ID NO:9).

Nucleotide 423–436 was altered from ATGCAATTTAAACT (SEQ ID NO:10) to CGGCAATTTAACGG (SEQ ID NO:11) using the mutagenic primer 141222:

141222: GGT ATT GTC CTG CAG ACG GCA ATT TAA CGG CTT CTG CGA ATC GC (SEQ ID NO:12).

The resulting plasmid was termed pMT 2188.

Growth Conditions

A strain of *Malbranchea cinnamomea* was cultivated in 500 ml shakeflasks on a medium containing 30 g wheat bran and 45 ml of the following solution: 4 g Yeast Extract, 1 g $KH_2PO_4$, 0.5 g $MgSO_4$ $7H_2O$, 15 g Glucose, 1000 ml tap water (Autoclave at 121° C. for 30 min), and the fungal mycelium was harvested after 3 days of growth. The harvested mycelium was immediately frozen in liquid $N_2$ and stored at −80° C.

Construction of a EcoRI/NotI-directional cDNA Library From *Malbranchea Cinnaomea*

Total RNA was prepared by extraction with guanidinium thiocyanate followed by ultracentrifugation through a 5.7 M CsCl cushion (Chirgwin et al., 1979, *Biochemistry* 18: 5294–5299) using the following modifications. The frozen mycelium was ground in liquid $N_2$ to a fine powder with a mortar and a pestle, followed by grinding in a precooled coffee mill, and immediately suspended in 5 volumes of RNA extraction buffer (4 M guanidinium thiocyanate, 0.5% sodium laurylsarcosine, 25 mM sodium citrate pH 7.0, 0.1 M β-mercaptoethanol). The mixture was stirred for 30 minutes at room temperature and centrifuged (20 minutes at 10 000 rpm, Beckman) to pellet the cell debris. The supernatant was collected, carefully layered onto a 5.7 M CsCl cushion (5.7 M CsCl, 10 mM EDTA, pH 7.5, 0.1% DEPC; autoclaved prior to use) using 26.5 ml supernatant per 12.0 ml of CsCl cushion, and centrifuged to obtain the total RNA (Beckman, SW 28 rotor, 25 000 rpm, room temperature, 24 hours). After centrifugation the supernatant was carefully removed and the bottom of the tube containing the RNA pellet was cut off and rinsed with 70% ethanol. The total RNA pellet was transferred to an Eppendorf tube, suspended in 500 ?l of TE, pH 7.6 (if difficult, heat occasionally for 5 minutes at 65° C.), phenol extracted, and precipitated with ethanol for 12 hours at −20° C. (2.5 volumes of ethanol, 0.1 volume of 3M sodium acetate pH 5.2). The RNA was collected by centrifugation, washed in 70% ethanol, and resuspended in a minimum volume of DEPC. The RNA concentration was determined by measuring $OD_{260/280}$.

The poly(A)$^+$ RNA was isolated by oligo(dT)-cellulose affinity chromatography (Aviv & Leder, 1972, *Proceedings of the National Academy of Sciences USA* 69: 1408–1412). A total of 0.2 g of oligo(dT) cellulose (Boehringer Mannheim, Indianapolis, Ind.) was preswollen in 10 ml of 1× of column loading buffer (20 mM Tris-Cl, pH 7.6, 0.5 M NaCl, 1 mM EDTA, 0.1% SDS), loaded onto a DEPC-treated, plugged plastic column (Poly Prep Chromatography Column, BioRad, Hercules, Calif.), and equilibrated with 20 ml of 1× loading buffer. The total RNA (1–2 mg) was heated at 65° C. for 8 minutes, quenched on ice for 5 minutes, and after addition of 1 volume of 2× column loading buffer to the RNA sample loaded onto the column. The eluate was collected and reloaded 2–3 times by heating the sample as above and quenching on ice prior to each loading. The oligo(dT) column was washed with 10 volumes of 1× loading buffer, then with 3 volumes of medium salt buffer (20 mM Tris-Cl, pH 7.6, 0.1 M NaCl, 1 mM EDTA, 0.1% SDS), followed by elution of the poly(A)$^+$ RNA with 3 volumes of elution buffer (10 mM Tris-Cl, pH 7.6, 1 mM EDTA, 0.05% SDS) preheated to 65° C., by collecting 500 μl fractions. The $OD_{260}$ was read for each collected fraction, and the mRNA containing fractions were pooled and ethanol precipitated at −20° C. for 12 hours. The poly(A)$^+$ RNA was collected by centrifugation, resuspended in DEPC-DIW and stored in 5–10 μg aliquots at −80° C.

Double-stranded cDNA was synthesized from 5 μg of *Malbranchea cinnamomea* poly(A)$^+$ RNA by the RNase H method (Gubler and Hoffman 1983, supra; Sambrook et al., 1989, supra) using a hair-pin modification. The poly(A)$^+$RNA (5 ?g in 5 ?l of DEPC-treated water) was heated at 70° C. for 8 minutes in a pre-siliconized, RNase-free Eppendorf tube, quenched on ice, and combined in a final volume of 50 μl with reverse transcriptase buffer (50 mM Tris-Cl pH 8.3, 75 mM KCl, 3 mM $MgCl_2$, 10 mM DTT) containing 1 mM of DATP, dGTP and dTTP, and 0.5 mM of 5-methyl-dCTP, 40 units of human placental ribonuclease inhibitor, 4.81 μg of oligo$(dT)_{18}$-NotI primer (Amersham-Pharmacia Biotech, Uppsala, Sweden) and 1000 units of SuperScript II reverse transcriptase (Gibco-BRL, USA).

First-strand cDNA was synthesized by incubating the reaction mixture at 45° C. for 1 hour. After synthesis, the mRNA:cDNA hybrid mixture was gel filtrated through a Pharmacia MicroSpin S-400 HR spin column according to the manufacturer's instructions.

After the gel filtration, the hybrids were diluted in 250 μl of second strand buffer (20 mM Tris-Cl pH 7.4, 90 mM KCl, 4.6 mM $MgCl_2$, 10 mM $(NH_4)_2SO_4$, 0.16 mM $\beta NAD^+$) containing 200 μM of each dNTP, 60 units of *E. coli* DNA polymerase I (Pharmacia, Uppsala, Sweden), 5.25 units of RNase H, and 15 units of *E. coli* DNA ligase. Second strand cDNA synthesis was performed by incubating the reaction tube at 16° C. for 2 hours, and an additional 15 minutes at 25° C. The reaction was stopped by addition of EDTA to 20 mM final concentration followed by phenol and chloroform extractions.

The double-stranded cDNA was ethanol precipitated at −20° C. for 12 hours by addition of 2 volumes of 96% ethanol and 0.2 volume of 10 M ammonium acetate, recovered by centrifugation, washed in 70% ethanol, dried (SpeedVac), and resuspended in 30 μl of Mung bean nuclease buffer (30 mM sodium acetate pH 4.6, 300 mM NaCl, 1 mM $ZnSO_4$, 0.35 mM dithiothreitol, 2% glycerol) containing 25 units of Mung bean nuclease. The single-stranded hair-pin DNA was clipped by incubating the reaction at 30° C. for 30 minutes, followed by addition of 70 μl of 10 mM Tris-Cl, pH 7.5, 1 mM EDTA, phenol extraction, and ethanol precipitation with 2 volumes of 96% ethanol and 0.1 volume 3 M sodium acetate pH 5.2 on ice for 30 minutes.

The double-stranded cDNAs were recovered by centrifugation (20,000 rpm, 30 minutes), and blunt-ended with T4 DNA polymerase in 30 μl of T4 DNA polymerase buffer (20 mM Tris-acetate, pH 7.9, 10 mM magnesium acetate, 50 mM potassium acetate, 1 mM dithiothreitol) containing 0.5 mM of each dNTP, and 5 units of T4 DNA polymerase by incubating the reaction mixture at +16° C. for 1 hour. The reaction was stopped by addition of EDTA to 20 mM final concentration, followed by phenol and chloroform extractions and ethanol precipitation for 12 h at −20° C. by adding 2 volumes of 96% ethanol and 0.1 volume of 3M sodium acetate pH 5.2.

After the fill-in reaction the cDNAs were recovered by centrifugation as above, washed in 70% ethanol, and the DNA pellet was dried in a SpeedVac. The cDNA pellet was resuspended in 25 ?l of ligation buffer (30 mM Tris-Cl, pH 7.8, 10 mM $MgCl_2$, 10 mM dithiothreitol, 0.5 mM ATP) containing 2 μg EcoRI adaptors (0.2 μg/μl, Pharmacia, Uppsala, Sweden) and 20 units of T4 ligase by incubating the reaction mix at 16° C. for 12 hours. The reaction was stopped by heating at 65° C. for 20 minutes, and then placed on ice for 5 minutes. The adapted cDNA was digested with NotI by addition of 20 μl autoclaved water, 5 μl of 10× NotI restriction enzyme buffer and 50 units of NotI, followed by incubation for 3 hours at 37° C. The reaction was stopped by heating the sample at 65° C. for 15 minutes. The cDNAs were size-fractionated by agarose gel electrophoresis on a 0.8% SeaPlaque GTG low melting temperature agarose gel (FMC, Rockland, Me.) in 1× TBE (in autoclaved water) to separate unligated adaptors and small cDNAs. The gel was run for 12 hours at 15 V, and the cDNA was size-selected with a cut-off at 0.7 kb by cutting out the lower part of the agarose gel. Then a 1.5% agarose gel was poured in front of the cDNA-containing gel, and the double-stranded cDNAs were concentrated by running the gel backwards until it appeared as a compressed band on the gel. The cDNA-containing gel piece was cut out from the gel and the cDNA was extracted from the gel using the GFX gel band purification kit (Amersham, Arlington Heights, Ill.) as follows. The trimmed gel slice was weighed in a 2 ml Biopure Eppendorf tube, then 10 ml of Capture Buffer was added for each 10 mg of gel slice, the gel slice was dissolved by incubation at 60° C. for 10 minutes, until the agarose was completely solubilized, the sample at the bottom of the tube by brief centrifugation. The melted sample was transferred to the GFX spin column placed in a collection tube, incubated at 25° C. for 1 minite, and then spun at full speed in a microcentrifuge for 30 seconds. The flow-through was discarded, and the column was washed with 500 μl of wash buffer, followed by centrifugation at full speed for 30 seconds. The collection tube was discarded, and the column was placed in a 1.5 ml Eppendorf tube, followed by elution of the cDNA by addition of 50 μl of TE pH 7.5 to the center of the column, incubation at 25° C. for 1 minute, and finally by centrifugation for 1 minute at maximum speed. The eluted cDNA was stored at −20° C. until library construction.

A plasmid DNA preparation for a EcoRI-NotI insert-containing pYES2.0 cDNA clone, was purified using a QIAGEN Tip-100 according to the manufacturer's instructions (QIAGEN, Valencia, Calif.). A total of 10 μg of purified plasmid DNA was digested to completion with NotI and EcoRI in a total volume of 60 μl by addition of 6 μl of 10× NEBuffer for EcoRI (New England Biolabs, Beverly, Mass.), 40 units of NotI, and 20 units of EcoRI followed by incubation for 6 hours at 37° C. The reaction was stopped by heating the sample at 65° C. for 20 minutes. The digested plasmid DNA was extracted once with phenol-chloroform, then with chloroform, followed by ethanol precipitation for 12 hours at −20° C. by adding 2 volumes of 96% ethanol and 0.1 volume of 3 M sodium acetate pH 5.2. The precipitated DNA was resuspended in 25 μl of 1× TE pH 7.5, loaded on a 0.8% SeaKem agarose gel in 1× TBE, and run on the gel for 3 hours at 60 V. The digested vector was cut out from the gel, and the DNA was extracted from the gel using the GFX gel band purification kit (Amersham-Pharmacia Biotech, Uppsala, Sweden) according to the manufacturer's instructions. After measuring the DNA concentration by $OD_{260/280}$, the eluted vector was stored at −20° C. until library construction.

To establish the optimal ligation conditions for the cDNA library, four test ligations were carried out in 10 μl of ligation buffer (30 mM Tris-Cl pH 7.8, 10 mM $MgCl_2$, 10 mM DTT, 0.5 mM ATP) containing 7 μl of double-stranded cDNA, (corresponding to approximately 1/10 of the total volume in the cDNA sample), 2 units of T4 ligase, and 25 ng, 50 ng and 75 ng of EcoRI-NotI cleaved pYES2.0 vector, respectively (Invitrogen). The vector background control ligation reaction contained 75 ng of EcoRI-NotI cleaved pYES.0 vector without cDNA. The ligation reactions were performed by incubation at 16° C. for 12 hours, heated at 65° C. for 20 minutes, and then 10 μl of autoclaved water was added to each tube. One μl of the ligation mixtures was electroporated (200 W, 2.5 kV, 25 mF) to 40 μl electrocompetent *E. coli* DH10B cells (Life Technologies, Gaithersburg, Md.). After addition of 1 ml SOC to each transformation mix, the cells were grown at 37° C. for 1 hour, 50 μl and 5 μl from each electroporation were plated on LB plates supplemented with ampicillin at 100 μg per ml and grown at 37° C. for 12 hours. Using the optimal conditions, a *Malbranchea cinnamomea* cDNA library containing $2\times10^7$ independent colony forming units was established in *E. coli*, with a vector background of ca. 1%. The cDNA library was stored as (1) individual pools (25,000 c.f.u./pool) in 20% glycerol at −80° C.; (2) cell pellets of the same pools at −20° C.; (3) Qiagen purified plasmid DNA from individual pools at −20° C. (Qiagen Tip 100); and (4) directional, double-stranded cDNA at −20° C.

Generation of a cDNA Probe for the Family 12 Xyloglucanase Using Polymeric-chain-reaction (PCT)

About twenty (20) nanograms of directional, double-stranded cDNA from *Malbranchea cinnamomea* was PCR amplified using 200 pmol of a degenerate deoxyinosine-containing oligonucleotide sense primer, corresponding to a peptide within the $NH_2$-terminus of the purified xyloglucanase (5'-GA(C/T) TT(C/T) TG(C/T) GGI CA(A/G) TGG GA-3') (SEQ ID NO:13) combined with 200 pmol of the antisense primer, corresponding to a peptide within an internal amino acid sequence determined from the purified xyloglucanase (5'-TGI (C/G) (A/T) (C/T) TG(A/G) TCC ATI CC(C/T) TG(C/T) TC-3') (SEQ ID NO:14), a PTC-200 Peltier Thermal cycler (MJ Research, USA) and 2.5 units of AmpliTaq Gold polymerase (Perkin-Elmer, USA). Polymerase-chain-reaction was performed by initiating the PCR by a denaturation step at 94° C. for 10 min, and then by 40 cycles of PCR using a cycle profile of denaturation at 94° C. for 30 sec, annealing at 55° C. for 30 sec, and extension at 72° C. for 1 min. The amplification products were analyzed by electrophoresis in a 2% agarose gel, and subsequently a ca. 0.6 kb PCR fragment was extracted from the gel using the GFX gel band purification kit (Amersham-Pharmacia Biotech, Uppsala, Sweden) according to the manufacturer's instructions. The purified PCR fragment was sequenced directly by the dideoxy chain-termination method (Sanger, F., Nicklen, S., and Coulson, A. R. (1977) Proc. Natl. Acad. Sci. U.S.A. 74, 5463–5467) using 300 ng of GFX-purified template, the Taq deoxy-terminal cycle sequencing kit (Perkin-Elmer, USA), fluorescent labeled terminators and 5 pmol of the degenerate deoxyinosine-containing oligonucleotide primer (5'-ACI GA (C/T) ATI CA(A/G) AA(C/T) GA(A/G) GA(A/G) (C/T)TI TGG-3' (SEQ ID NO:15). Analysis of the sequence data was performed according to Devereux et al., 1984 (Devereux, J., Haeberli, P., and Smithies, O. (1984) Nucleic Acids Res. 12, 387–395).

Screening of the cDNA Library 30 000 colony-forming units from the *Malbranchea cinnamomea* CDNA library constructed in pYES 2.0 were screened by colony hybridization (Sambrook et al. (1989) Molecular cloning: A laboratory manual, Cold Spring Harbor lab., Cold Spring Harbor, N.Y.) in *E. coli* using a random-primed (Feinberg, A. P., and Vogelstein, B. (1983) Anal. Biochem. 132, 6–13) $^{32}P$-labeled (>$1\times10^9$ cpm/μg) PCR product for the xyloglucanase as a probe. The hybridizations were carried out in 2×SSC (Sambrook et al. (1989) Molecular cloning: A laboratory manual, Cold Spring Harbor lab., Cold Spring Harbor, N.Y.), 5×Denhardt's solution (Sambrook et al. (1989) Molecular cloning: A laboratory manual, Cold Spring Harbor lab., Cold Spring Harbor, N.Y.), 0.5% (w/v) SDS, 100 μg/ml denatured salmon sperm DNA for 20 h at 65° C. followed by washes in 5×SSC at 25° C. (2×15 min), 2×SSC, 0.5% SDS at 65° C. (30 min), 0.2×SSC, 0.5% SDS at 65° C. (30 min) and finally in 5×SSC (2×15 min) at 25° C. Screening of the *Malbranchea cinnamomea* cDNA library yielded 4 strongly hybridizing clones, which were further analyzed by sequencing the cDNA ends with pYES forward and reverse polylinker primers (Invitrogen, USA), and determining the nucleotide sequence of the longest xyloglucanase cDNA (designated pC1XYG1011) from both strands.

Nucleotide Sequence Analysis

The nucleotide sequence of the full-length *Malbranchea cinnamomea* xyloglucanase cDNA clone pC1XYG1011 was determined from both strands by the dideoxy chain-termination method (Sanger, F., Nicklen, S., and Coulson, A. R. (1977) Proc. Natl. Acad. Sci. U.S.A. .74, 5463–5467) using 500 ng of Qiagen-purified template (Qiagen, USA), the Taq deoxy-terminal cycle sequencing kit (Perkin-Elmer, USA), fluorescent labeled terminators and 5 pmol of either PYES 2.0 polylinker primers (Invitrogen, USA) or synthetic oligonucleotide primers, resulting in the appended sequence SEQ ID NO:1 and the deduced amino acid sequence of the family 12 xyloglucanase precursor shown in appended SEQ ID NO:2. Analysis of the sequence data was performed according to Devereux et al., 1984 (Devereux, J., Haeberli, P., and Smithies, O. (1984) Nucleic Acids Res. 12, 387–395).

Heterologous Expression in *Aspergillus Oryzae*

Transformation of *Aspergillus oryzae*

Transformation of *Aspergillus oryzae* was carried out as described by Christensen et al., (1988), Biotechnology 6, 1419–1422.

Construction of the Xyloglucanase Expression Cassette for *Aspergillus expression*

Plasmid DNA was isolated from the *Malbranchea cinnamomea* cDNA clone pC1XYG1011 using standard procedures and analyzed by restriction enzyme analysis. The XYG1011 cDNA insert was PCR amplified using 50 ng of pC1XYG1011 plasmid DNA as template, 100 pmol of the sense primer (SEQ ID NO:16) (5'-CGGGATCCGATAGAGTCGAG-ATGAAGG-3'), combined with 100 pmol of the antisense primer (5'-CCGCTCGAGCCAA-AGAGCTAAAAAAGTTG-3') (SEQ ID NO:17), a PTC-200 Peltier Thermal cycler (MJ Research, USA) and the Expand High Fidelity PCR System (Roche Molecular Biochemicals, Germany) according to the manufacturer's instructions. Thirty cycles of PCR was performed using a cycle profile of denaturation at 94° C. for 30 sec, annealing at 60° C. for 30 sec, and extension at 72° C. for 2 min. The amplification products were analyzed by electrophoresis in a 1% agarose gel, and subsequently the ca. 1.0 kb XYG1011 PCR fragment was extracted from the gel using the GFX gel band purification kit (Amersham- Pharmacia Biotech, Uppsala, Sweden) according to the manufacturer's instructions. Both the purified PCR fragment and Aspergillus expression vector pMT2188 were double digested with BamHI and XhoI. The vector was subsequently dephosphorylated with Shrimp alkaline phosphatase (Roche, Mannheim, Germany) following the manufacturers instructions. The restriction enzymes and phosphatase were removed by phenol and chloroform extraction, and the PCR fragment was ligated to the vector using standard methods (Sambrook et al. 1989). *E. coli* strain DB6507 ($F^-$, pyrF74::Tn5, supE44, lacY1, ara14, galK2, xyl5, mtl1, leuB6, proA2, hsdS20, recA13, rpsL20, thi-1, $?^-$) was transformed with the ligation mixture, and tranformants were screened for presence of the PCR insert in pMT2188 by colony PCR. Colony PCR reactions were performed using the standard PCR method (Saiki et al., 1988, Science 239:487–491) with a 10?l volume, unlysed *E. coli* cells providing the template, an annealing temperature of 55° C. and primers with the following sequences:

primer1: GTTTCCAACTCAATTTACCTC (SEQ ID NO:18)

primer2: TTGCCCTCATCCCCATCCTTT (SEQ ID NO:19)

An expression clone thus identified was designated pMStr43, and the sequence of the cloned PCR fragment was determined to insure that no errors were introduced during amplification. A single C to T substitution was found downstream from the stop codon at position 849.

Transformation of *Aspergillus oryzae*

General procedure: 100 ml of YPD (Sherman et al., Methods in Yeast Genetics, Cold Spring Harbor Laboratory, 1981) is inoculated with spores of *A. oryzae* and incubated with shaking at 37° C. for about 2 days. The mycelium is harvested by filtration through miracloth and washed with 200 ml of 0.6 M $MgSO_4$. The mycelium is suspended in 15 ml of 1.2 M $MgSO_4$ with 10 mM $NaH_2PO_4$, pH 5.8, and 1 ml of the same buffer containing 120 mg of Novozym 234 is added, and the mixture is incubated with gentle agitation for 1.5–2.5 hours at 37° C. until a large number of protoplasts are visible in a sample inspected with a microscope. The suspension is filtered through miracloth, the filtrate transferred to a sterile tube and overlaid with 5 ml of 0.6 M sorbitol, 100 mM Tris-HCl, pH 7.0. Centrifugation is performed for 15 minutes at 100 g and the protoplasts are collected from the top of the $MgSO_4$ cushion. 2 volumes of STC (1.2M sorbitol, 10 mM $CaCl_2$, 10 mM tris-HCl, pH 7.5) are added to the protoplast suspension and the mixture is centrifuged for 5 minutes at 1000 g. The protoplast pellet is resuspended in 3 ml of STC and repelleted. This is repeated. Finally the protoplasts are resuspended in 0.2–1 ml of STC. 100 μl of protoplast suspension is mixed with 5 μg of the transforming DNA suspended in 10 μl of STC. The mixture is left at room temperature for 25 minutes. 1 ml of 60% PEG 4000 in 10 mM CaCl2 and 10 mM Tris-HCl, pH 7.5 is added and gently mixed. The mixture is incubated at room temperature for 25 minutes, then spun at 2500 g for 15 minutes. The pelleted protoplasts are resuspended in 1 ml of STC and spread on selective medium containing 1.0M sucrose for osmotic support of the protoplasts. For pMT2188, a minimal medium with 10 mM acetamide and 67 mM CsCl provides selection for the amds marker. Transformants are distinguishable after incubation for 4–7 days at 37° C.

Identification and Isolation of a Xyloglucanase-producing Aspergillus Oryzae Transformant Each colony arising on selective medium following transformation of Aspergillus was tested for xyloglucanase production by transferring conidia to solid minimal medium adjusted to pH 7.5 and containing 1% glucose and 10 mM $NaNO_3$, and with a thin overlay of the same containing 0.1% w/v of the substrate AZCL-xyloglucan (Megazyme, Bray, Ireland). Hydrolysis of the substrate was detected by visible diffusion of blue azurine dye after overnight growth of the conidia at 37° C. One transformant produced xyloglucanase as detected in this assay.

This transformant was isolated by dilution streaking conidia on selective medium containing 0.01% triton X-100 to limit colony size. Four isolated colonies appearing to arise from single spores were retested for xyloglucanase activity on the medium described above, and additionally were grown in 10 ml of YP medium (Sherman et al., Methods in Yeast Genetics, Cold Spring Harbor Laboratory, 1981) with 2% maltose at 30° C. and 200 revolutions/minute for 2 days. Supernatants from these cultures were fractionated by SDS/PAGE using a 12% Tris-glycine polyacrylamide gel (Novex, San Diego, Calif., USA) and protein was stained with Coumassie-blue according to the manufacturers instructions. The Aspergillus isolate producing the greatest amount of xyloglucanase was designated MStr125.

Determination of Xyloglucanase Units (XGU or XyloU)

The xyloglucanase activity is measured using AZCL-xyloglucan from Megazyme, Ireland, as substrate.

A solution of 0.2% of the blue substrate is suspended in a 0.1 M phosphate buffer pH 7.5 under stirring. The solution is distributed under stirring to 1.5 ml Eppendorf tubes (0.75 ml to each), 50 μl enzyme solution is added and they are incubated in an Eppendorf Thermomixer model 5436 for 20 min. at 40° C. with a mixing of 1200 rpm. After incubation the coloured solution is separated from the solid by 4 min. centrifugation at 14,000 rpm and the absorbance of the supernatant is measured at 600 nm. The assay is done in duplicates and the background done in duplicates is subtracted. The reading at 600 nm has to be between 0.2 and 1.5 for use in calculation of catalytic activity.

One XyloU unit is defined as the amount of enzyme resulting in an absorbance of 0.24 in a 1 cm cuvette at 600 nm.

The following examples illustrate the invention.

EXAMPLE 1

Screening for Microorganisms Producing Alkaline Xyloglucanase

The fungal microorganisms *Malbranchea cinnamomea*, CBS 960.72, *Malbranchea cinnamomea*, CBS343.55 and *Malbranchea cinnamomea*, UAMH 2485 were cultured as described in the Materials and Methods section. The culture broths were tested for xyloglucanase, beta-glucanase and cellulase activity in the agarose plate assay at three different pH (pH 3, pH 7, pH 10).

The following activities were found:

| | Xyloglucanase | | | Cellulase | | | β-Glucanase | | |
|---|---|---|---|---|---|---|---|---|---|
| Strain No. | pH3 | pH7 | pH10 | pH3 | pH7 | pH10 | pH | pH | pH10 |
| CBS960.72 | – | ++ | ++ | ++ | +++ | ++ | ++ | ++ | ++ |
| CBS343.55 | – | ++ | ++ | ++ | +++ | ++ | ++ | ++ | ++ |
| UAMH2485 | – | ++ | ++ | ++ | +++ | ++ | ++ | ++ | ++ |

EXAMPLE 2

Purification of Xyloglucanase from *Malbranchea cinnamomea*

A. Partial Purification

To separate the two types of cellulases from xyloglucanase in the respective culture broths obtained in example 1, xyloglucanase and cellulase were partially purified from culture broth from media A (see media list) by the method described under Materials and Methods.

About 500 ml of culture broth for each fungal strain was obtained by culturing the fungus in media A and then extraction by adding 100 ml of sterilized water. The culture broth was filtered and protein was precipitated by 80% ammonium sulfate. The precipitated protein pellets was dissolved in about 60 ml of 25 mM $KH_2PO_4$/NaOH buffer at pH 6.0. Then the sample was subjected to ultra-filtration (washed with the same buffer) on a Millipore Biomax-5 cellulase-resistent membrane with a cut off 5 kDa until the conductivity of the proteins was below 1 ms/cm. 10 ml of this sample was applied to ion-exchange column (Q-Sepharose Fast Flow, 34 ml) and equilibrated with 0.025 M phosphate buffer pH 6.0. Both xyloglucanase and CMCase bound to the column and was eluted using a 1N sodium chloride gradient. All fractions were collected and analyzed for xyloglucanase and cellulase activity by using microtiter plate assay with 0.5% AZCL-substrate.

Figure 2:
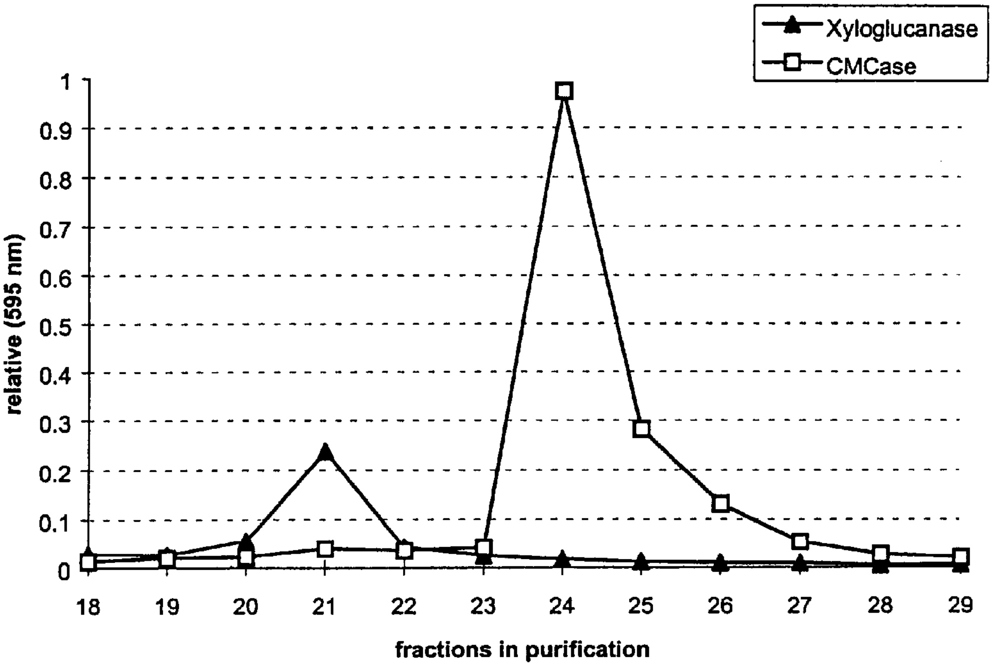
FIG. 2 shows the relative xyloglucanase and CMC-ase activity at 595 nm of the fractions from the strain UAMH2485.
Figure 3:
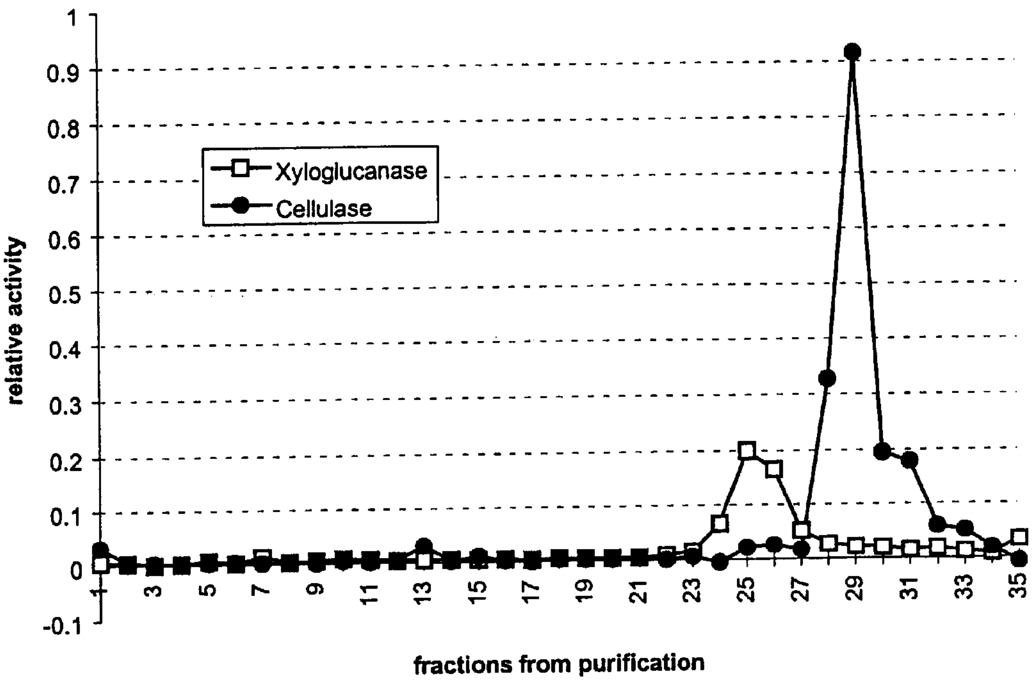
FIG. 3 shows the relative xyloglucanase and CMC-ase activity at 595 nm of the fractions from the strain CBS 343.55.
Figure 4:
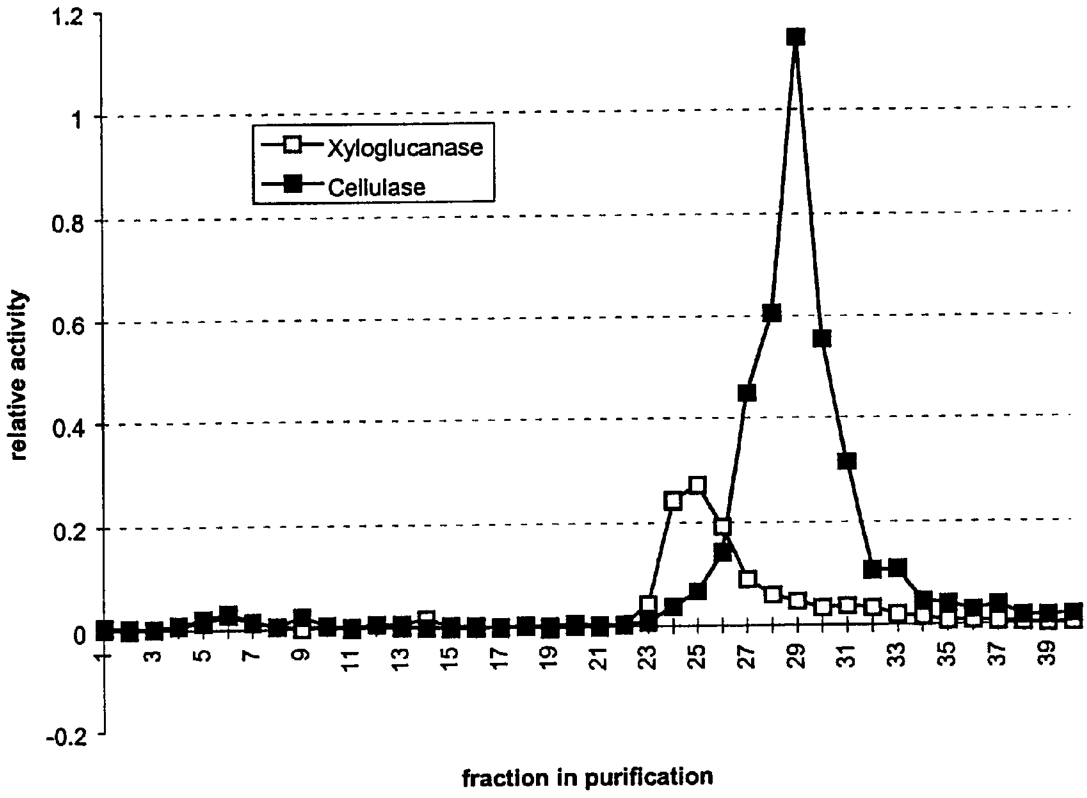
FIG. 4 shows the relative xyloglucanase and CMC-ase activity at 595 nm of the fractions from the strain CBS 960.72.

In FIGS. 1–3are shown the xyloglucanase and cellulase activity in different fractions from partial purification of each of the three strains of *Malbranchea cinnamomea*: FIG. 1 shows the fractions from the strain UAMH2485, FIG. 2 shows the fractions from the strain CBS 343.55, and FIG. 3 shows the fractions from the strain CBS 960.72. From the figures it can be seen that the two enzymes appeared in different fractions and thus were easily separated. 1–3 fractions contained most xyloglucanase activity and they have no cellulase activity on either agarose plate CMC (1%), AZCL-HE-cellulose (0.1%) even after overnight incubation at 45° C. or liquid assay (0.5% AZCL-HE-cellulose, pH7 and 9, 45° C., 800 rpm for 2 and half hours.

Fractions with xyloglucanase activity were pooled and concentrated by using a membrance with a cut-off of 10 kDa. Concentrated samples were used for IEF assay to determine pI and SDS-page to determine the molecular weight. It was determined that the xyloglucanase from all three strains of Malbranchea cinnamomea has the same pI (around pH 3.5) and the same molecular weight (around 25 kDa). Further, the protein band was electroblotted and part of the N-terminal sequence was determined as FCGQXDSEQSGPYIVYNNL (SEQ ID NO:2), wherein X is probably W (tryptophan).

The xyloglucanase activity for each of the three xyloglucanases was determined as described under Materials and Methods with the following result:

| Strains | XGU/ml |
|---|---|
| CBS 960.72 | 27.5 |
| CBS 343.55 | 9.1 |
| UAMH 2485 | 12.3 |

B. Purification

Xyloglucanase from culture broth was partially purified as described above. Collected fractions with xyloglucanase activity were desalted by Hiprep 26/10 column, divided into plastic tubes (15 ml per tube) and lyophilised. The lyophilised powder was solubilized in 2 ml deionized water; 1 ml was used for characterization and 1 ml for further purification. The solution was diluted in 25 mM Tris buffer pH 7.0 followed by concentration on a Amicon cell with a membrane with a cut-off of 5 kDa for reducing the conductivity. When the conductivity was below 3 mSi the solution was applied to a 1 ml MonoQ column equilibrated with the same buffer. The xyloglucanase bound to the column and was eluted using a 0.5 M sodium chloride gradient. All fractions were analyzed for xyloglucanase activity and 2 fractions contained all the activity.

On an SDS-PAGE of the pooled fraction a clear band with a MW of 25 kDa could be identified. This protein band was electro-blotted and part of the N-terminal sequence determined and the following data obtained: FCGQXDSEQSGPYIVYNNL (SEQ ID NO:2). This partial N-terminal sequence has homology (63%) to *Tiasporella phaseolina* XET disclosed in the international patent publication WO98/38288.

The xyloglucanase active fractions showed no activity on AZCL HE cellulose after 2 hours incubation under identical conditions as the xyloglucanase assay described under Materials and Methods.

EXAMPLE 3

Characterisation of Xyloglucanase from *Malbranchea cinnamomea*, UAMH 2485, CBS 343.55 and CBS 960.72 pH Profiles

For the determination of pH profile of the xyloglucanases purified in example 2, a solution of 0.2% of the blue substrate AZCL-xyloglucan is suspended in a 0.1 M phosphate-citrate buffer (pH 3, 4, 5) or Borax/$NaH_2PO_4$ buffer for pH 6, MOPS for pH 7, HEPES for pH8, or glycine buffer for pH 9–11 under stirring and used for microtiter plate assay as described in Materials and Methods. 80 $\mu$l of 0.2% AZCL-xyloglucan substrate solution and 20 $\mu$l of partially purified xyloglucanase sample were mixed and incubated for 1 hour under 50° C., 800 rpm in an Eppendorf thermomixer. The pH profile for each of the xyloglucanases from *Malbrachea cinnamomea*, UAMH 2485, CBS 343.55 and CBS 960.72 is shown in the following table (in terms of relative xyloglucanase activity):

| pH | UAMH 2485 | CBS 343.55 | CBS 960.72 |
|---|---|---|---|
| 4 | 0.28 | 0.26 | 0.44 |
| 5 | 0.41 | 0.49 | 0.51 |
| 6 | 0.69 | 0.72 | 0.72 |
| 7 | 1 | 1 | 1 |
| 8 | 0.76 | 0.83 | 0.83 |
| 9 | 0.74 | 0.81 | 0.81 |
| 10 | 0.50 | 0.57 | 0.66 |
| 11 | 0.43 | 0.51 | 0.61 |

The result shows that the xyloglucanases from these strains have almost identical pH profiles. Compared with known xyloglucanases they have more alkaline activity: there was 50–80% relative xyloglucanase activity even at pH10.

Temperature Profiles

For the determination of temperature profiles, 70 μl of 0.2 of the blue substrate AZCL-xyloglucan solution suspended in 0.1 M glycine buffer pH 9 under stirring and 30 μl partially purified xyloglucanase sample were mixed in Eppendorf tube and incubated for 40 minutes at various temperature (20, 30, 40, 50, 60, and 70° C.) in water bath. Denatured enzyme sample (100° C. boiling for 20 min) was used as bland. After incubation the coloured solution is separated from the solid by centrifugation at 10000 rpm for 5 minutes at 40° C. 60 μl of supernatant was transferred into a microtiter plate and the absorbency is measured by BioRad Microplate Reader at 595 nm.

The temperature profiles of xyloglucanase from the strains *Malbranchea cinnamomea*, UAMH 2485, CBS 343.55 and CBS 960.72 is shown below (in terms of relative xyloglucanase activity):

| Temperature (° C.) | UAMH 2485 | CBS 343.55 | CBS 960.72 |
|---|---|---|---|
| 20 | 0.12 | 0.20 | 0.15 |
| 30 | 0.22 | 0.30 | 0.26 |
| 40 | 0.54 | 0.62 | 0.56 |
| 50 | 1 | 1 | 1 |
| 60 | 0.30 | 0.38 | 0.30 |
| 70 | 0.16 | 0.16 | 0.16 |

Xyloglucanases from the three *Malbranchea cinnamomea* strains have very similar temperature profiles, they are active from 20–70° C. and have optimum activity at a temperature around 50° C.

Thermostability

For thermostability test, the partially purified enzyme samples from example 2 were incubated in 40° C. water bath and sampled after different incubation time (0, 0.5, 1, 2, 3, 4, 5 and 6 hours), then the xyloglucanase activity from these samples were determined by microtiter plate assay by mixing 70 μl of 0.2% of the blue substrate AZCL-xyloglucan solution suspended in 0.1 M glycine buffer pH 9 under stirring and 30 μl sample in microtiter plate and incubated for 40 minutes at 50° C. 800 rpm in an Eppendorf thermomixer. Denatured enzyme sample (100° C. boiling for 20 min) was used as bland. After incubation the colored solution is separated from the solid by centrifugation at 10000 rpm for 5 minutes at 4° C. 60 μl of supernatant was transferred into a microtiter plate and the absorbency is measured by BioRad Microplate Reader at 595 nm.

The result of thermostability test is shown below (in terms of relative xyloglucanase activity):

| Incubation time (hr) | UAMH 2485 | CBS 343.55 | CBA 960.72 |
|---|---|---|---|
| 0 | 1 | 1 | 1 |
| 0.5 | 0.95 | 1 | 0.95 |
| 1 | 0.88 | 0.98 | 1.08 |
| 2 | 1 | 1.3 | 0.98 |
| 3 | 0.95 | 0.99 | 0.95 |
| 4 | 0.86 | 0.96 | 0.96 |
| 5 | 0.89 | 1 | 0.98 |
| 6 | n.a. | 1 | 1.01 |

It can be seen that the enzymes from the three *Malbranchea cinnamonea* rains are very stable at the tested condition. Hardly seen any activity lost even after 6 hours' incubation at 40° C.

Substrate Specificity

Partially purified xyloglucanase from the three *Malbranchea cinnamomea* strains UAMH2485, CBS 343.55 and CBS 960.72 were tested for substrate specificity by using different substrates, including AZCL-xyloglucan (Tamarind) for xyloglucanse, AZCL-Xylan (oat spelts) for xylanase, AZCL-debranched-Arabinan for aravinase, AZCL-Galactomannan (carob) for mannanase, AZCL-HE-Cellulose for cellulase, AZCL-Dextran for endo-1,6-a-glucanase, AZCL-Galactan (potato) for endo-1,4-β-galactanase.

It was found that partially purified xyloglucanase from these three *Malbranchea cinnamomea* strains only exhibited xyloglucanase activity and no other enzyme activity. It can be concluded that xyloglucanases from these *Malbranchea cinnamomea* strains are xyloglucan specific enzymes.

Detergent Compatibility

Partially purified xyloglucanase from the three *Malbranchea cinnamomea* strains UAMH2485, CBS 343.55 and CBS 960.72 as described in example 2 A were tested in 5 different commercial European and Chinese detergent compositions at two dosages (2 g/land 4 g/l): the European detergents branded Ariel® and Omo® and the Chinese detergents branded Ariel®, Tide® and Whitecat® in comparison with the xyloglucanase activity in buffer pH 7.

The purified xyloglucanases described in example 2 B were also tested in the following detergent compositions under normal conditions (40° C., 20 minutes incubation): Ariel®Future liquid , 6 g/l, 18 Grain Hardness; Ariel®Future powder, 6 g/l, 18 Grain Hardness; US Tide® liquid, 2 g/l, 8 Grain Hardness; US Tide® powder, 2 g/l, 8 Grain Hardness; Japanese liquid Bonus™, 0.65 g/l, 8 Grain Hardness; Japanese Ariel® powder, 0.65 g/l, 8 Grain Hardness; all relative to the activity in 0.1M phosphate buffer pH 7.5.

Xyloglucanases from all three strains were found to be fully active in all tested commercial detergents and in all the tested dosages.

EXAMPLE 4

Purification and Characterization of Xyloglucanase Cloned from *Malbranchea cinnamomea*

Fermentation broth from was obtained from batch #9947 using *Aspergillus oryzae* transformant Mstr125 (see Materials and Methods). Based on the sequence SEQ ID NO:2 the following data could be calculated: MW 25 kDa, pI 3.9, molar extinction coefficient 65530.

The fermentation broth was filtered through a Whatmann glass filter GF/D. and total 4700 ml with 515 Xylounits per ml was obtained.

The clear fermentation solution was concentrated and formulated with mono propylene glycol for performance evaluation.

A small sample was purified to high homogeneity using superdex75 column chromatography using 0.1 m Sodium acetate buffer pH 6.0. The pure enzyme gave a single band in SDS-PAGE with a apparent molecular weight of 25 kDa. Using DSC the melting temperature was found to be 74° C. The pure enzyme has a specific activity of 160 xylounits per mg protein.

Rabbit serum was raised against the pure enzyme using normal procedure at the Danish laboratory DAKO.

The N-terminal sequence of the mature enzyme was found to be ADFCGQXDSEQSGPYIVYNNLWN (SEQ ID NO:2) using edman degradation, the X could not be identified but is a W based on the sequence of the gene.

The enzyme was more than 50% active between pH 5.5 and 9.0 at 40° C. and fully active in commercial powder detergents. It was very stable in liquid detergent with a half-life above 30 days at 35° C.

The enzyme has no activity on CMC so it is not a cellulase.

LITERATURE

Cooney, D. & Emerson, R. 1964. Thermophilic fungi. An account of their biology, activites and classification. W. H. Freeman and Co., San Francisco and London, 188 pp.

Hawskworth, H. D. et al. 1995. Dictionary of the Fungi., IMI, CAB.

Pauly, M. et al. 1999 A xyloglucan-specific endo-β-1,4-glucanase from *Aspergillus aculeatus*: expression cloning in yeast, purification and characterization of the recombinant enzyme. Glycobiology 9: 93–100.

Mouchacca, J. 1997. Thermophilic fungi: biodiversity and taxonomic status. Cryptogamie, Mycol. 18: 19–69.

Oorschot, C. A. N. van & Hoog, G. S. de 1984. Some hyphomycetes with thallic conidia. Mycotaxon 20: 129–132.

Sigler, L. 1987. Trichothecium cinnamomeum, an earlier name for the thermophilic hyphomycete *Malbranchea sulphurea*. Mycologia 79: 142–143.

Sigler, L. & Carmichael, J. W. 1976. Taxonomy of Malbranchea and some other hyphomycetes with arthroconidia. Mycotaxon 4: 349–488.

Ausubel, F. M. et al. (eds.) "Current protocols in Molecular Biology". John Wiley and Sons, 1995.

N. C. Carpita and D. M. Gibeaut (1993) The Plant Journal 3:1–30.

T. Christensen et al. Biotechnology vol 6 page 1419–1422, 1988.

Devereux et al. (1984) Nucleic Acids Res. 12, 387–395.

Diderichsen, B., Wedsted, U., Hedegaard, L., Jensen, B. R., Sjøholm, C. (1990) Cloning of aldB, which encodes alpha-acetolactate decarboxylase, an exoenzyme from *Bacillus brevis*. J. Bacteriol. 172:4315–4321.

Dretzen, G., Bellard, M., Sassone-Corsi, P., Chambon, P. (1981) A reliable method for the recovery of DNA fragments from agarose and acrylamide gels. Anal. Biochem., 112, 295–298.

Eriksson, O. E. & Hawksworth, D. L.: Systema Ascomycetum vol 12 (1993).

S. C. Fry et al (1992) Biochemical Journal 282:821–828

Hawksworth, D. L., Kirk, P. M., Sutton, B. C. and Pegler, D. N.: Dictionary of the fungi, International Mycological Institute, 616 pp (1995);

T. Hayashi and D. P. Delmer (1988) Carbohydrate Research 181:273–277.

Henrissat, B. 1991. A classification of glycosyl hydrolases based on amino acid sequence similaritites. Biochem. J., 280:309–316.

Henrissat, B., and A. Bairoch. 1993. New families in the classification of glycosyl hydrolases based on amino acid sequence similaritites. Biochem. J., 293:781–788.

Jülich, W.: Higher Taxa of Basidiomycetes, Bibliotheca Mycologia 85, 485 pp (1981).

Jørgensen, P. L. et al., 1990, Gene, 96, p. 37–41.

McKenzie, T. et al., 1986, Plasmid 15:93–103.

Leatherbarrow, R. J. (1992) Grafit version 3.0 Erithacus Software Ltd. Staines, U. K.

Lever, M. (1972) A new reaction for colormetric determination of carbohydrates. Anal. Biochem. 47, 273–279.

O'Donnell, K.:Zygomycetes in culture, University of Georgia, US, 257 pp (1979).

Pitcher, D. G., Saunders, N. A., Owen, R. J. (1989). Rapid extraction of bacterial genomic DNA with guanidium thiocyanate. Lett. Appl. Microbiol., 8, 151–156.

J. K. C. Rose et al (1996) Plant Physiology 110:493–499

A. L. Sonenshein, J. A. Hoch and Richard Losick (Eds.) (1993) *Bacillus subtilis* and other Gram-Positive Bacteria, American Society for microbiology, p.618.

Vincken, J. P., Beldman, G., and Voragen, A. G. J. Substrate-specificity of endoglucanases—what determines xyloglucanase activity. *Carbohydrate Research* 298(4) :299–310, 1997.

Von Arx, J. A.: The genera of fungi sporulating in culture, 424 pp (1981).

R. L. Whistler and J. N. BeMiller (1993) Industrial gums: Polysaccharides and their derivatives, Academic Press Inc.

Yasbin, R. E., Wilson, G. A. and Young, F. E. (1975) Transformation and transfection in lysogenic strains of *Bacillus subtilis*: evidence for selective induction of prophage in competent cells. J. Bacteriol, 121:296–304.

W. S. York et al (1996) Carbohydrate Research 285:99–128.

What is claimed is:

1. An isolated or purified polypeptide having xyloglucanase activity which is obtained from a strain of Malbranchea and has (a) xyloglucanase activity throughout the pH range of 4–11, measured at 50° C.;

(b) a molecular mass of 25+/−10 kDa, as determined by SDS-PAGE;

(c) an isoelectric point in the range of 3–5; and (d) an N-terminal sequence of Ala-Asp-Phe-Cys-Gly-Gln-Trp-Asp-Ser-Glu-Gln-Ser-Gly-Pro-Tyr-Ile-Val-Tyr-Asn-Asn-Leu (amino acid residues 29–49 of SEQ ID NO: 2).

2. The isolated or purified polypeptide of claim 1, which is obtained from a strain of a species selected from the group consisting of *Malbranchea albolutea, Malbranchea arcuata, Malbranchea aurantiaca, Malbranchea bolognesii-chiurcoi, Malbranchea chrysosporioidea, Malbranchea cinnamomea* (and the synonyms *Malbranchea sulfurea, Malbranchea pulchella* var. *sulfurea* and *Thermoidium sulfureum*), *Malbranchea circinata, Malbranchea dendritica, Malbranchea filamentosa, Malbranchea flava, Malbranchea flavorosea, Malbranchea flocciformis, Malbranchea fulva, Malbranchea graminicola, Malbranchea gypsea, Malbranchea kambayashii, Malbranchea multicolor, Malbranchea pulchella, Malbranchea sclerotica*, and *Malbranchea setosa.*

3. The isolated or purified polypeptide of claim 2, wherein the strain is a *Malbranchea cinnamomea* strain.

4. The isolated or purified polypeptide of claim 3, wherein the strain is selected from the group consisting of *Malbranchea cinnamomea*, CBS 115.68; *Malbranchea cinnamomea*, CBS 343.55; *Malbranchea cinnamomea*, CBS 423.54; *Malbranchea cinnamomea*, CBS 960.72; *Malbranchea cinnamomea*, MUCL 9500; *Malbranchea cinnamomea*, MUCL 11291; and *Malbranchea cinnamomea*, UAMH 3827.

5. The isolated or purified polypeptide of claim 1, wherein the polypeptide exhibits a relative xyloglucanase activity of at least 50% at pH 9.5 or of at least 40% at pH 10, compared to the activity at the pH optimum.

6. The isolated or purified polypeptide of claim 1, wherein the polypeptide belongs to family 12 of glycosyl hydrolases.

7. The isolated or purified polypeptide of claim 1, which exhibits no activity on carboxymethylcellulose (CMC) or microcrystalline cellulose (Avicel).

8. An enzyme preparation comprising the isolated or purified polypeptide of claim 1.

9. The preparation of claim 8, which further comprises one or more enzymes selected from the group consisting of alpha-amylases, cellobiohydrolases, cellulases (endoglucanases), cutinases, beta-glucanases, glucoamylases, hemicellulases, laccases, ligninases, lipases, other mannanases, oxidases, pectate lyases, pectinases, peroxidases, pectin acetyl esterases, pectin lyases, pectin methylesterases, phenoloxidases, polygalacturonases, proteases, pullulanases, reductases, rhamnogalacturonases, transglutaminases, xylanases, xyloglucanases, or mixtures thereof.

10. A detergent composition comprising a polypeptide of claim 1 and a surfactant.

11. A process for machine treatment of a fabric, comprising treating the fabric with a washing solution containing the polypeptide of claim 1.

12. A method of producing the polypeptide of claim 1, comprising (a) culturing a strain of Malbranchea under conditions permitting the production of the xyloglucanase enzyme, and (b) recovering the polypeptide from the culture.

13. An isolated or purified family 12 xyloglucanase selected from the group consisting of (a) a polypeptide comprising a fragment encoded by the DNA sequence of positions 141–806 of SEQ ID NO:1;

(b) a polypeptide produced by culturing a cell comprising the sequence of SEQ ID NO:1 under conditions wherein the DNA sequence is expressed;

(c) a polypeptide having a sequence of at least 80% identity to positions 29–250 of SEQ ID NO:2 wherein the identity is determined by GAP provided in the GCG program package version 10.0 using a GAP creation penalty of 8 and GAP extension penalty of 2.

14. The xyloglucanase of claim 13, which comprises an amino acid sequence of SEQ ID NO: 2.

15. The xyloglucanase of claim 13, which comprises an amino acid sequence of amino acid residues 29–250 of SEQ ID NO: 2.

16. An isolated xyloglucanase which is (i) free from homologous impurities, and (ii) produced by culturing a cell comprising a DNA sequence of positions 141–806 of SEQ ID NO:1.

* * * * *